US012678388B2

(12) United States Patent
Rapaport et al.

(10) Patent No.: US 12,678,388 B2
(45) Date of Patent: Jul. 14, 2026

(54) DERMATOLOGICAL COMPOSITIONS AND USE THEREOF

(71) Applicant: BONE SCI. BIO LTD., Beer-Sheva (IL)

(72) Inventors: Yaron Rapaport, Lehavim (IL); Noa Harduf, Kibutz Gevim (IL); Hanna Rapaport, Lehavim (IL)

(73) Assignee: BONE SCI. BIO LTD., Beer-Sheva (IL)

( * ) Notice: Subject to any disclaimer, the term of this patent is extended or adjusted under 35 U.S.C. 154(b) by 307 days.

(21) Appl. No.: 18/551,350

(22) PCT Filed: Mar. 20, 2022

(86) PCT No.: PCT/IL2022/050309
§ 371 (c)(1),
(2) Date: Sep. 19, 2023

(87) PCT Pub. No.: WO2022/201146
PCT Pub. Date: Sep. 29, 2022

(65) Prior Publication Data
US 2024/0165006 A1     May 23, 2024

Related U.S. Application Data

(60) Provisional application No. 63/163,887, filed on Mar. 21, 2021.

(51) Int. Cl.
| | |
|---|---|
| *A61K 8/64* | (2006.01) |
| *A61K 9/00* | (2006.01) |
| *A61K 38/08* | (2019.01) |
| *A61K 38/10* | (2006.01) |
| *A61K 38/16* | (2006.01) |
| *A61L 27/26* | (2006.01) |
| *A61L 27/36* | (2006.01) |
| *A61L 27/38* | (2006.01) |
| *A61L 27/52* | (2006.01) |

(52) U.S. Cl.
CPC .............. *A61K 8/64* (2013.01); *A61K 9/0014* (2013.01); *A61K 38/08* (2013.01); *A61K 38/10* (2013.01); *A61K 38/16* (2013.01); *A61L 27/26* (2013.01); *A61L 27/36* (2013.01); *A61L 27/3834* (2013.01); *A61L 27/52* (2013.01); *A61L 2300/252* (2013.01); *A61L 2400/06* (2013.01); *A61L 2430/04* (2013.01); *A61L 2430/34* (2013.01)

(58) Field of Classification Search
CPC ........ A61K 8/64; A61K 9/0014; A61K 38/08; A61K 38/10; A61K 38/16; A61L 27/26; A61L 27/36; A61L 27/3834; A61L 27/52; A61L 2300/252; A61L 2400/06; A61L 2430/04; A61L 2430/34
See application file for complete search history.

(56) References Cited

U.S. PATENT DOCUMENTS

2011/0008406 A1     1/2011     Altman

FOREIGN PATENT DOCUMENTS

| | | | |
|---|---|---|---|
| EP | 2552938 B1 | 3/2016 | |
| WO | WO-2006014570 A2 * | 2/2006 | .............. A61P 35/00 |
| WO | 2007148334 A1 | 12/2007 | |
| WO | WO-2009072119 A2 * | 6/2009 | .............. A61K 38/03 |
| WO | WO-2014104981 A1 * | 7/2014 | ......... C07K 5/06034 |

OTHER PUBLICATIONS

Amosi N (2011) Peptide Based Hydrogels Act as a Calcium Reservoir and Combined with Mineral for Improved Bone Tissue Regeneration (Thesis, Ben-Gurion University of the Negev). http://aranne5.bgu.ac.il/others/AmosiNadav.pdf. 89 pages.
Amosi et al., (2012) Acidic peptide hydrogel scaffolds enhance calcium phosphate mineral turnover into bone tissue. Acta Biomater 8(7): 2466-2475.
Bitter et al., (1987) Expression and secretion vectors for yeast. Methods Enzymol 153: 516-544.
Brisson et al., (1984) Expression of a bacterial gene in plants by using a viral vector. Nature 310: 511-514.
Broglie et al., (1984) Light-regulated expression of a pea ribulose-1,5-bisphosphate carboxylase small subunit gene in transformed plant cells. Science 224(4651): 838-843.
Coruzzi et al., (1984) Tissue-specific and light-regulated expression of a pea nuclear gene encoding the small subunit of ribulose-1,5-bisphosphate carboxylase. EMBO J 3(8): 1671-1679.
Gurley et al., (1986) Upstream sequences required for efficient expression of a soybean heat shock gene. Mol Cell Biol 6(2): 559-565.
Jeong et al., (2017) Hyaluronic acid-hydroxyapatite nanocomposite hydrogels for enhanced biophysical and biological performance in a dermal matrix. J Biomed Mater Res A 105(12): 3315-3325.
La Gatta et al., (2019) Hyaluronan-based hydrogels as dermal fillers: The biophysical properties that translate into a "volumetric" effect. PLoS One 14(6): e0218287.
La Gatta et al., (2020) Hyaluronan Dermal Fillers: Efforts Towards a Wider Biophysical Characterization and the Correlation of the Biophysical Parameters to the Clinical Outcome. Clin Cosmet Investig Dermatol 13: 87-97.
Larrañeta et al., (2016) Microneedle arrays as transdermal and intradermal drug delivery systems: Materials science, manufacture and commercial development. Materials Science and Engineering: R: Reports 104: 1-32.

(Continued)

*Primary Examiner* — Robert A Wax
*Assistant Examiner* — John W Lippert, III
(74) *Attorney, Agent, or Firm* — Allan A. Fanucci, Esq.

(57) ABSTRACT

Dermatological compositions comprising amphiphilic peptides, derivatives or salts thereof are provided. The compositions are particularly useful as dermal fillers and for inducing soft tissue repair and regeneration.

26 Claims, 18 Drawing Sheets

Specification includes a Sequence Listing.

(56) References Cited

OTHER PUBLICATIONS

Meng et al., (2009) The effect of a self-assembling peptide nanofiber scaffold (peptide) when used as a wound dressing for the treatment of deep second degree burns in rats. J Biomed Mater Res B Appl Biomater 89(2): 379-391.

Nakamura et al., (2018) Alternative test models for skin ageing research. Exp Dermatol 27(5): 495-500.

Rapaport et al., (2000) Two-Dimensional Order in β-Sheet Peptide Monolayers. J Am Chem Soc 122(50): 12523-12529.

Rapaport et al., (2002) Assembly of Triple-Stranded β-Sheet Peptides at Interfaces. J Am Chem Soc 124(32): 9342-9343.

Rapaport et al., (2008) Hydrogel Scaffolds of Amphiphilic and Acidic β-Sheet Peptides. Advanced Functional Materials 18(19): 2889-2896.

Segman-Magidovich et al., (2008) Matrices of Acidic β-Sheet Peptides as Templates for Calcium Phosphate Mineralization. Advanced Materials 20(11): 2156-2161.

Studier et al., (1990) Use of T7 RNA polymerase to direct expression of cloned genes. Methods Enzymol 185: 60-89.

Sundaram et al., (2015) Cohesivity of Hyaluronic Acid Fillers: Development and Clinical Implications of a Novel Assay, Pilot Validation with a Five-Point Grading Scale, and Evaluation of Six U.S. Food and Drug Administration—Approved Fillers. Plast Reconstr Surg 136(4): 678-686.

Takamatsu et al., (1987) Expression of bacterial chloramphenicol acetyltransferase gene in tobacco plants mediated by TMV-RNA. EMBO J 6(2): 307-311.

Van Nieuwenhove et al., (2017) Soft tissue fillers for adipose tissue regeneration: From hydrogel development toward clinical applications. Acta Biomater 63: 37-49.

Zarzhitsky and Rapaport (2011) The interactions between doxorubicin and amphiphilic and acidic β-sheet peptides towards drug delivery hydrogels. J Colloid Interface Sci 360(2): 525-531.

Zarzhitsky et al., (2013) The effect of pH and calcium ions on the stability of amphiphilic and anionic β-sheet peptide hydrogels. Biopolymers 100(6): 760-772.

American Cancer Society. Breast Cancer Facts & Figure 2019-2020. Atlanta: American Cancer Society, Inc. 2019. (https://www.cancer.org/content/dam/cancer-org/research/cancer-facts-and-statistics/breast-cancer-facts-and-figures/breast-cancer-facts-and-figures-2019-2020.pdf). 44 pages.

Chang et al. (2011), "Cell Responses to Surface and Architecture of Tissue Engineering Scaffolds," In: Regenerative Medicine and Tissue Engineering—Cells and Biomaterials. InTechOpen. DOI: 10.5772/21983. pp. 569-588.

* cited by examiner

● PFD5 - G'              O PFD5 - G''

▲ HA syringe- G'         ✕ HA syringe- G''

● PFD5              ▲ HA syringe

| 1.5% | 2.0% | 2.5% | 3.0% | 3.5% | 5.0% |

T=0          T=5 s'          T=30 s'          T=60 s'          T=90s'

T=0          T=5 s'          T=30 s'          T=60 s'          T=90s'

T=0          T=5 s'          T=30 s'          T=60 s'          T=90s'

T<sub>0</sub>

+ 200% serum                + 300% serum                + 400% serum

T<sub>0</sub>

+ 200% serum                + 300% serum                + 400% serum

▲ 2.5% PFD5 - G'        ■ HA1 - G'        ● 2.5% PFD5 + HA1 - G'

○ 2.5% PFD5 - G''        + HA1 - G''        ✕ 2.5% PFD5 + HA1 - G''

✕ 2.5% PFD5　　▲ HA1　　o 2.5% PFD5 + HA1

SEQUENCE LISTING

<160> NUMBER OF SEQ ID NOS: 36

<210> SEQ ID NO 1
<211> LENGTH: 13
<212> TYPE: PRT
<213> ORGANISM: Artificial Sequence
<220> FEATURE:
<223> OTHER INFORMATION: PFD5, peptide

<400> SEQUENCE: 1

```
Pro Asp Phe Asp Phe Asp Phe Asp Phe Asp Phe Asp Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: peptide

<400> SEQUENCE: 2

Pro Glu Phe Glu Phe Glu Phe Glu Phe Glu Phe Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: peptide

<400> SEQUENCE: 3

Glu Phe Glu Phe Glu Phe Glu Phe Glu Phe Glu Pro
1               5                   10

<210> SEQ ID NO 4
<211> LENGTH: 13
<212> TYPE: PRT
<213> ORGANISM: Artificial Sequence
<220> FEATURE:
<223> OTHER INFORMATION: peptide

<400> SEQUENCE: 4

Pro Ser Phe Ser Phe Ser Phe Ser Phe Ser Phe Ser Pro
1               5                   10

<210> SEQ ID NO 5
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Phosphoserine
<220> FEATURE:
<221> NAME/KEY: MISC_FEATURE
<222> LOCATION: (4)..(4)
<223> OTHER INFORMATION: Phosphoserine
<220> FEATURE:
<221> NAME/KEY: MISC_FEATURE
<222> LOCATION: (6)..(6)
<223> OTHER INFORMATION: Phosphoserine
<220> FEATURE:
<221> NAME/KEY: MISC_FEATURE
<222> LOCATION: (8)..(8)
<223> OTHER INFORMATION: Phosphoserine
<220> FEATURE:
<221> NAME/KEY: MISC_FEATURE
<222> LOCATION: (10)..(10)
<223> OTHER INFORMATION: Phosphoserine
<220> FEATURE:
<221> NAME/KEY: MISC_FEATURE
<222> LOCATION: (12)..(12)
<223> OTHER INFORMATION: Phosphoserine

<400> SEQUENCE: 5

Pro Ser Phe Ser Phe Ser Phe Ser Phe Ser Phe Ser Pro
1               5                   10
```

```
<210> SEQ ID NO 6
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Phosphotyrosine
<220> FEATURE:
<221> NAME/KEY: MISC_FEATURE
<222> LOCATION: (4)..(4)
<223> OTHER INFORMATION: Phosphotyrosine
<220> FEATURE:
<221> NAME/KEY: MISC_FEATURE
<222> LOCATION: (6)..(6)
<223> OTHER INFORMATION: Phosphotyrosine
<220> FEATURE:
<221> NAME/KEY: MISC_FEATURE
<222> LOCATION: (8)..(8)
<223> OTHER INFORMATION: Phosphotyrosine
<220> FEATURE:
<221> NAME/KEY: MISC_FEATURE
<222> LOCATION: (10)..(10)
<223> OTHER INFORMATION: Phosphotyrosine
<220> FEATURE:
<221> NAME/KEY: MISC_FEATURE
<222> LOCATION: (12)..(12)
<223> OTHER INFORMATION: Phosphotyrosine

<400> SEQUENCE: 6

Pro Tyr Phe Tyr Phe Tyr Phe Tyr Phe Tyr Phe Tyr Pro
1               5                   10

<210> SEQ ID NO 7
<211> LENGTH: 13
<212> TYPE: PRT
<213> ORGANISM: Artificial Sequence
<220> FEATURE:
<223> OTHER INFORMATION: peptide

<400> SEQUENCE: 7

Pro Glu Leu Glu Leu Glu Leu Glu Leu Glu Leu Glu Pro
1               5                   10

<210> SEQ ID NO 8
<211> LENGTH: 13
<212> TYPE: PRT
<213> ORGANISM: Artificial Sequence
<220> FEATURE:
<223> OTHER INFORMATION: peptide

<400> SEQUENCE: 8

Pro Asp Leu Asp Leu Asp Leu Asp Leu Asp Leu Asp Pro
1               5                   10

<210> SEQ ID NO 9
<211> LENGTH: 13
<212> TYPE: PRT
<213> ORGANISM: Artificial Sequence
<220> FEATURE:
<223> OTHER INFORMATION: peptide

<400> SEQUENCE: 9

Pro Ser Leu Ser Leu Ser Leu Ser Leu Ser Leu Ser Pro
1               5                   10

<210> SEQ ID NO 10
<211> LENGTH: 13
```

```
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Phosphoserine
<220> FEATURE:
<221> NAME/KEY: MISC_FEATURE
<222> LOCATION: (4)..(4)
<223> OTHER INFORMATION: Phosphoserine
<220> FEATURE:
<221> NAME/KEY: MISC_FEATURE
<222> LOCATION: (6)..(6)
<223> OTHER INFORMATION: Phosphoserine
<220> FEATURE:
<221> NAME/KEY: MISC_FEATURE
<222> LOCATION: (8)..(8)
<223> OTHER INFORMATION: Phosphoserine
<220> FEATURE:
<221> NAME/KEY: MISC_FEATURE
<222> LOCATION: (10)..(10)
<223> OTHER INFORMATION: Phosphoserine
<220> FEATURE:
<221> NAME/KEY: MISC_FEATURE
<222> LOCATION: (12)..(12)
<223> OTHER INFORMATION: Phosphoserine

<400> SEQUENCE: 10

Pro Ser Leu Ser Leu Ser Leu Ser Leu Ser Leu Ser Pro
1               5                   10

<210> SEQ ID NO 11
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Phosphotyrosine
<220> FEATURE:
<221> NAME/KEY: MISC_FEATURE
<222> LOCATION: (4)..(4)
<223> OTHER INFORMATION: Phosphotyrosine
<220> FEATURE:
<221> NAME/KEY: MISC_FEATURE
<222> LOCATION: (6)..(6)
<223> OTHER INFORMATION: Phosphotyrosine
<220> FEATURE:
<221> NAME/KEY: MISC_FEATURE
<222> LOCATION: (8)..(8)
<223> OTHER INFORMATION: Phosphotyrosine
<220> FEATURE:
<221> NAME/KEY: MISC_FEATURE
<222> LOCATION: (10)..(10)
<223> OTHER INFORMATION: Phosphotyrosine
<220> FEATURE:
<221> NAME/KEY: MISC_FEATURE
<222> LOCATION: (12)..(12)
<223> OTHER INFORMATION: Phosphotyrosine

<400> SEQUENCE: 11

Pro Tyr Leu Tyr Leu Tyr Leu Tyr Leu Tyr Leu Tyr Pro
1               5                   10

<210> SEQ ID NO 12
<211> LENGTH: 19
<212> TYPE: PRT
<213> ORGANISM: Artificial Sequence
<220> FEATURE:
<223> OTHER INFORMATION: peptide
```

-continued

<400> SEQUENCE: 12

```
Pro Glu Phe Ser Phe Glu Phe Ser Phe Glu Phe Ser Phe Glu Phe Ser
1               5                   10                  15

Phe Glu Pro
```

<210> SEQ ID NO 13
<211> LENGTH: 19
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Phosphoserine
<220> FEATURE:
<221> NAME/KEY: MISC_FEATURE
<222> LOCATION: (6)..(6)
<223> OTHER INFORMATION: Phosphoserine
<220> FEATURE:
<221> NAME/KEY: MISC_FEATURE
<222> LOCATION: (10)..(10)
<223> OTHER INFORMATION: Phosphoserine
<220> FEATURE:
<221> NAME/KEY: MISC_FEATURE
<222> LOCATION: (14)..(14)
<223> OTHER INFORMATION: Phosphoserine

<400> SEQUENCE: 13

```
Pro Ser Phe Ser Phe Ser Phe Ser Phe Ser Phe Ser Phe Ser Phe Ser
1               5                   10                  15

Phe Ser Pro
```

<210> SEQ ID NO 14
<211> LENGTH: 19
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Phosphoserine
<220> FEATURE:
<221> NAME/KEY: MISC_FEATURE
<222> LOCATION: (6)..(6)
<223> OTHER INFORMATION: Phosphoserine
<220> FEATURE:
<221> NAME/KEY: MISC_FEATURE
<222> LOCATION: (10)..(10)
<223> OTHER INFORMATION: Phosphoserine
<220> FEATURE:
<221> NAME/KEY: MISC_FEATURE
<222> LOCATION: (14)..(14)
<223> OTHER INFORMATION: Phosphoserine

<400> SEQUENCE: 14

```
Pro Ser Phe Glu Phe Ser Phe Glu Phe Ser Phe Glu Phe Ser Phe Glu
1               5                   10                  15

Phe Glu Pro
```

<210> SEQ ID NO 15
<211> LENGTH: 19
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)

```
<223> OTHER INFORMATION: Phosphoserine
<220> FEATURE:
<221> NAME/KEY: MISC_FEATURE
<222> LOCATION: (6)..(6)
<223> OTHER INFORMATION: Phosphoserine
<220> FEATURE:
<221> NAME/KEY: MISC_FEATURE
<222> LOCATION: (10)..(10)
<223> OTHER INFORMATION: Phosphoserine
<220> FEATURE:
<221> NAME/KEY: MISC_FEATURE
<222> LOCATION: (14)..(14)
<223> OTHER INFORMATION: Phosphoserine

<400> SEQUENCE: 15

Pro Ser Phe Asp Phe Ser Phe Asp Phe Ser Phe Asp Phe Ser Phe Asp
1               5                   10                  15

Phe Asp Pro

<210> SEQ ID NO 16
<211> LENGTH: 30
<212> TYPE: PRT
<213> ORGANISM: Artificial Sequence
<220> FEATURE:
<223> OTHER INFORMATION: peptide

<400> SEQUENCE: 16

Ala Leu Glu Phe Glu Phe Glu Phe Glu Pro Ala Glu Phe Glu Phe Glu
1               5                   10                  15

Phe Glu Leu Pro Ala Leu Glu Phe Glu Phe Glu Phe Glu Pro
            20                  25                  30

<210> SEQ ID NO 17
<211> LENGTH: 13
<212> TYPE: PRT
<213> ORGANISM: Artificial Sequence
<220> FEATURE:
<223> OTHER INFORMATION: peptide

<400> SEQUENCE: 17

Pro Glu Phe Glu Phe Glu Lys Glu Phe Glu Phe Glu Pro
1               5                   10

<210> SEQ ID NO 18
<211> LENGTH: 19
<212> TYPE: PRT
<213> ORGANISM: Artificial Sequence
<220> FEATURE:
<223> OTHER INFORMATION: peptide

<400> SEQUENCE: 18

Pro Glu Phe Glu Phe Glu Phe Glu Phe Glu Phe Glu Gly Gly Gly Arg
1               5                   10                  15

Gly Asp Ser

<210> SEQ ID NO 19
<211> LENGTH: 14
<212> TYPE: PRT
<213> ORGANISM: Artificial Sequence
<220> FEATURE:
<223> OTHER INFORMATION: peptide

<400> SEQUENCE: 19

Phe Glu Phe Glu Phe Glu Pro Gly Gly Gly Arg Gly Asp Ser
1               5                   10
```

```
<210> SEQ ID NO 20
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: acetylation of the amino terminus
<220> FEATURE:
<221> NAME/KEY: MISC_FEATURE
<222> LOCATION: (13)..(13)
<223> OTHER INFORMATION: amidation of the carboxy terminus

<400> SEQUENCE: 20

Pro Asp Phe Asp Phe Asp Phe Asp Phe Asp Phe Asp Pro
1               5                   10

<210> SEQ ID NO 21
<211> LENGTH: 14
<212> TYPE: PRT
<213> ORGANISM: Artificial Sequence
<220> FEATURE:
<223> OTHER INFORMATION: peptide

<400> SEQUENCE: 21

Pro Asp Phe Asp Phe Asp Phe Asp Phe Asp Phe Asp Phe Asp
1               5                   10

<210> SEQ ID NO 22
<211> LENGTH: 12
<212> TYPE: PRT
<213> ORGANISM: Artificial Sequence
<220> FEATURE:
<223> OTHER INFORMATION: peptide

<400> SEQUENCE: 22

Phe Asp Phe Asp Phe Asp Phe Asp Phe Asp Phe Asp
1               5                   10

<210> SEQ ID NO 23
<211> LENGTH: 13
<212> TYPE: PRT
<213> ORGANISM: Artificial Sequence
<220> FEATURE:
<223> OTHER INFORMATION: peptide

<400> SEQUENCE: 23

Pro Glu Phe Glu Phe Glu Phe Glu Phe Glu Phe Glu Pro
1               5                   10

<210> SEQ ID NO 24
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (13)..(13)
<223> OTHER INFORMATION: amidation of the carboxy terminus

<400> SEQUENCE: 24

Pro Asp Phe Asp Phe Asp Phe Asp Phe Asp Phe Asp Pro
1               5                   10

<210> SEQ ID NO 25
<211> LENGTH: 10
```

-continued

```
<212> TYPE: PRT
<213> ORGANISM: Artificial Sequence
<220> FEATURE:
<223> OTHER INFORMATION: peptide

<400> SEQUENCE: 25

Phe Glu Phe Glu Phe Glu Phe Glu Phe Glu
1               5                   10

<210> SEQ ID NO 26
<211> LENGTH: 12
<212> TYPE: PRT
<213> ORGANISM: Artificial Sequence
<220> FEATURE:
<223> OTHER INFORMATION: peptide

<400> SEQUENCE: 26

Phe Glu Phe Glu Phe Glu Phe Glu Phe Glu Phe Glu
1               5                   10

<210> SEQ ID NO 27
<211> LENGTH: 14
<212> TYPE: PRT
<213> ORGANISM: Artificial Sequence
<220> FEATURE:
<223> OTHER INFORMATION: peptide

<400> SEQUENCE: 27

Phe Glu Phe Glu Phe Glu Phe Glu Phe Glu Phe Glu Phe Glu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: peptide

<400> SEQUENCE: 28

Pro Asp Phe Asp Phe Asp Phe Asp Phe Asp
1               5                   10

<210> SEQ ID NO 29
<211> LENGTH: 14
<212> TYPE: PRT
<213> ORGANISM: Artificial Sequence
<220> FEATURE:
<223> OTHER INFORMATION: peptide

<400> SEQUENCE: 29

Pro Asp Phe Asp Phe Asp Phe Asp Phe Asp Phe Asp Phe Asp
1               5                   10

<210> SEQ ID NO 30
<211> LENGTH: 18
<212> TYPE: PRT
<213> ORGANISM: Artificial Sequence
<220> FEATURE:
<223> OTHER INFORMATION: peptide

<400> SEQUENCE: 30

Pro Asp Phe Asp Phe Asp Phe Asp Phe Asp Phe Asp Phe Asp Phe Asp
1               5                   10                  15

Phe Asp

<210> SEQ ID NO 31
```

<211> LENGTH: 10
<212> TYPE: PRT
<213> ORGANISM: Artificial Sequence
<220> FEATURE:
<223> OTHER INFORMATION: peptide

<400> SEQUENCE: 31

Phe Asp Phe Asp Phe Asp Phe Asp Phe Asp
1               5                   10

<210> SEQ ID NO 32
<211> LENGTH: 12
<212> TYPE: PRT
<213> ORGANISM: Artificial Sequence
<220> FEATURE:
<223> OTHER INFORMATION: peptide

<400> SEQUENCE: 32

Phe Asp Phe Asp Phe Asp Phe Asp Phe Asp Phe Asp
1               5                   10

<210> SEQ ID NO 33
<211> LENGTH: 14
<212> TYPE: PRT
<213> ORGANISM: Artificial Sequence
<220> FEATURE:
<223> OTHER INFORMATION: peptide

<400> SEQUENCE: 33

Phe Asp Phe Asp Phe Asp Phe Asp Phe Asp Phe Asp Phe Asp
1               5                   10

<210> SEQ ID NO 34
<211> LENGTH: 17
<212> TYPE: PRT
<213> ORGANISM: Artificial Sequence
<220> FEATURE:
<223> OTHER INFORMATION: peptide

<400> SEQUENCE: 34

Pro Asp Phe Asp Phe Asp Phe Asp Phe Asp Phe Asp Pro Arg Gly Asp
1               5                   10                  15

Ser

<210> SEQ ID NO 35
<211> LENGTH: 8
<212> TYPE: PRT
<213> ORGANISM: Artificial Sequence
<220> FEATURE:
<223> OTHER INFORMATION: peptide

<400> SEQUENCE: 35

Pro Phe Asp Phe Asp Phe Asp Pro
1               5

<210> SEQ ID NO 36
<211> LENGTH: 15
<212> TYPE: PRT
<213> ORGANISM: Artificial Sequence
<220> FEATURE:
<223> OTHER INFORMATION: peptide

<400> SEQUENCE: 36

Pro Phe Asp Phe Asp Phe Asp Pro Gly Gly Gly Arg Gly Asp Ser
1               5                   10                  15

DERMATOLOGICAL COMPOSITIONS AND USE THEREOF

RELATED APPLICATIONS

This application is a Section 371 national phase filing of PCT Application No. PCT/IL2022/050309, filed on Mar. 20, 2022, and titled DERMATOLOGICAL COMPOSITIONS AND USE THEREOF, which claims the benefit of U.S. Provisional Patent Application No. 63/163,887, filed on Mar. 21, 2021, both of which are incorporated by reference herein in their entireties.

SEQUENCE LISTING

Sequences described herein are also presented in a text file named BNSC_003PCT_ST25.txt (size: 11 kbytes), the content of which is hereby incorporated by reference herein in its entirety.

FIELD OF THE INVENTION

The present invention relates to dermatological compositions comprising at least one amphiphilic peptide, derivative or salt thereof. The present invention further relates to methods of use of the dermatological compositions as dermal fillers and for soft tissue repair and regeneration.

BACKGROUND OF THE INVENTION

Amphiphilic peptides, composed of pairs of hydrophobic-hydrophilic alternating amino acid residues self-assemble to form β-sheet structures (Rapaport et al. JACS, 2000, 122: 12523-12529; Rapaport et al. JACS, 2002, 124:9342-9343). These structures are characterized by the presence of pleated β-strands that are interlinked by hydrogen bonds and other molecular interactions between amino acid side chains. Amphiphilic peptides that tend to form the β-sheet structure have been shown to assemble into hydrogels suitable for drug delivery as well as for the formation of biocompatible matrices for tissue engineering (Rapaport et al. Adv. Func. Mater. 2008, 18(19):2889-2896; Segman-Magidovich et al. Adv. Mater. 2008, 20:2156-2161; Amosi et al. Acta Biomater. 2012, 8:2466-2475; Zarzhitsky et al. J. Coll. Int. Sci. 2011, 360:525-531).

Zarzhitsky et al. (Biopolymers, 2013, 100(6):760-72) describes the effect of peptide concentration, pH, and calcium ions concentration on the self-assembly of amphiphilic and anionic β-sheet peptide hydrogels. The mechanical stability and resistance to dissolution were shown to be highly linked to these factors.

WO 2007/148334 describes amphiphilic peptides comprising predominantly acidic amino acids, which are capable, alone or in combination with ions and minerals, of forming hydrogels at physiological pH and serving as scaffolds for mineralization.

WO 2009/072119 describes therapeutic uses of amphiphilic peptides and pharmaceutical compositions comprising them for treatment and prevention of progression of osteoporosis and pre-osteoporotic conditions by direct administration into deficient, deteriorated or injured bone and in particular into low bone mineral density sites. The amphiphilic peptides comprise predominantly acidic amino acids, which are capable, alone or in combination with ions and minerals, of forming β-sheet assemblies and hydrogels at physiological pH and serve as scaffolds for mineralization directly at the bone site.

Jeong et al. (J. Biomed. Mater. Res. A, 2017, 105(12): 3315-3325) describes a hyaluronic acid (HAc)-hydroxyapatite (HAp) nanocomposite (HAc-nanoHAp) hydrogel as compared to pure HAc hydrogel for soft tissue augmentation application. HAc-nanoHAp was shown to provide great improvement to wrinkles because of its higher stiffness and gel cohesiveness in comparison with that of pure HAc. HAc-nanoHAp also presented great enhancement in strengthening the dermal matrix by stimulating the synthesis of collagen and elastin.

EP 2552938 describes an amphiphilic linear peptide and/or peptoid capable of forming a hydrogel. The peptides/peptoids include short amphiphilic sequences with a hydrophobic portion of aliphatic amino acids and at least one acidic, neutral, or basic polar amino acid. A plurality of such peptides/peptoids assembles to supramolecular helical fibers and forms peptide hydrogels after assembly.

There remains a yet unmet need for compositions suitable for dermatological use.

SUMMARY OF THE INVENTION

The present invention provides dermatological compositions comprising at least one amphiphilic peptide comprising alternating hydrophobic/hydrophilic amino acid residues, or a derivative or a salt thereof, wherein the hydrophilic amino acid residues are predominantly acidic. The compositions are useful as dermatological fillers, in effecting an improvement in skin appearance and texture and in treating various skin disorders and soft tissue defects.

The present invention is based, in part, on the unexpected finding that amphiphilic peptides comprising alternating hydrophobic/hydrophilic amino acid residues, in which the hydrophilic amino acid residues are predominantly acidic, can form stable hydrogels suitable as dermal or soft tissue fillers. Furthermore, the amphiphilic peptides of the present invention were shown to exert osteoblast and endothelial cell adhesion with structural similarity to fibrin(ogen) scaffolds. Accordingly, it is now disclosed for the first time that the peptides and compositions comprising same are useful in treating various skin conditions such as wounds, burns, surgical cuts, etc. The compositions of the present invention were further compared to commercially available dermal fillers which are composed of crosslinked hyaluronic acid and were shown to have superior properties as compared to those of hyaluronic-acid based products in term of cohesivity, swellability, viscoelasticity, rheology, injectability, biocompatibility, and resistance to degradation. As such, the compositions are useful for soft tissue augmentation, for example, in the treatment of soft tissue defects including face and body contouring.

According to one aspect of the present invention, there is provided a dermatological composition comprising at least one amphiphilic peptide comprising alternating hydrophobic/hydrophilic amino acid residues, or a derivative or a salt thereof, wherein the peptide comprises 1-20 pairs of hydrophobic-hydrophilic alternating amino acid residues wherein the hydrophilic amino acid residue is selected from the group consisting of a negatively charged amino acid, a hydroxyl-containing amino acid, and a phosphorylated-hydroxyl-containing amino acid, and wherein said peptide has no more than 10% positively charged amino acid residues, and a dermatologically acceptable carrier.

According to one embodiment, the dermatological composition is a soft tissue filler composition. According to another embodiment, the dermatological composition is a topical composition for use in treating a skin condition. According to yet another embodiment, the dermatological composition is a cosmetic composition.

According to some embodiments, the at least one amphiphilic peptide is 2 to 40 amino acids in length. According to certain embodiments, the at least one amphiphilic peptide is 7 to 28 amino acids in length. According to additional embodiments, the peptide further comprises at least one terminal Proline (Pro) residue. According to various embodiments, the peptide further comprises two terminal Pro residues. According to some embodiments, the hydrophobic amino acid is selected from the group consisting of Phenylalanine (Phe), Leucine (Leu), Isoleucine (Ile), Valine (Val), Tryptophan (Trp), and Alanine (Ala). Each possibility represents a separate embodiment. According to certain embodiments, the hydrophobic amino acid is Phe or Leu. Each possibility represents a separate embodiment. According to some embodiments, the hydrophilic amino acid is selected from the group consisting of Glutamic acid (Glu), Aspartic acid (Asp), Tyrosine (Tyr), Serine (Ser), Threonine (Thr), Phosphoserine (Ser(PO$_4$)), Phosphothreonine (Thr(PO$_4$)), and Phosphotyrosine (Tyr(PO$_4$)). Each possibility represents a separate embodiment.

According to another embodiment, the peptide comprises an amino acid sequence according to Formula I:

X-(hydrophobic-hydrophilic)$_n$-B      (Formula I)

or a salt thereof, wherein n designates an integer from 1 to 20, hydrophobic designates a hydrophobic amino acid residue, hydrophilic designates a hydrophilic amino acid residue, X designates Pro, Pro-hydrophilic or the peptide's amino terminus, and B designates Pro or the peptide's carboxy terminus. Each possibility represents a separate embodiment.

According to various embodiments, the amino terminus is modified. In one embodiment, the amino terminus is acetylated. According to other embodiments, the carboxy terminus is modified. In one embodiment, the carboxy terminus is amidated.

According to particular embodiments, the peptide comprises an amino acid sequence of any of the following formulae X-(Phe-Glu)$_n$-B, X-(Phe-Asp)$_n$-B, X-(Leu-Glu)$_n$-B, and X-(Leu-Asp)$_n$-B or a salt thereof, wherein n designates an integer from 1 to 20, X designates Pro, Pro-hydrophilic amino acid residue, or the peptide's amino terminus, and B designates Pro or the peptide's carboxy terminus. Each possibility represents a separate embodiment.

According to specific embodiments, the peptide comprises a sequence selected from the group consisting of:

(SEQ ID NO: 1)
Pro-(Asp-Phe)$_5$-Asp-Pro, (SEQ ID NO: 2)
Pro-Glu-(Phe-Glu)$_5$, (SEQ ID NO: 3)
Glu-(Phe-Glu)$_5$-Pro, (SEQ ID NO: 4)
Pro-(Ser-Phe)$_5$-Ser-Pro, (SEQ ID NO: 5)
Pro-(SerPO$_4$-Phe)$_5$-SerPO$_4$-Pro, (SEQ ID NO: 6)
Pro-(TyrPO$_4$-Phe)$_5$-TyrPO$_4$-Pro,

4

-continued (SEQ ID NO: 7)
Pro-(Glu-Leu)$_5$-Glu-Pro, (SEQ ID NO: 8)
Pro-(Asp-Leu)$_5$-Asp-Pro, (SEQ ID NO: 9)
Pro-(Ser-Leu)$_5$-Ser-Pro, (SEQ ID NO: 10)
Pro-(SerPO$_4$-Leu)$_5$-SerPO$_4$-Pro, (SEQ ID NO: 11)
Pro-(TyrPO$_4$-Leu)$_5$-TyrPO$_4$-Pro, (SEQ ID NO: 12)
Pro-(Glu-Phe-Ser-Phe)$_4$-Glu-Pro, (SEQ ID NO: 13)
Pro-(SerPO$_4$-Phe-Ser-Phe)$_4$-Ser-Pro, (SEQ ID NO: 14)
Pro-(SerPO$_4$-Phe-Glu-Phe)$_4$-Glu-Pro, (SEQ ID NO: 15)
Pro-(SerPO$_4$-Phe-Asp-Phe)$_4$-Asp-Pro, (SEQ ID NO: 16)
Ala-Leu-Glu-(Phe-Glu)$_3$-Pro-Ala-(Glu-Phe)$_3$-Glu-Leu-Pro-Ala-Leu-Glu-(Phe-Glu)$_3$-Pro, (SEQ ID NO: 17)
Pro-Glu-(Phe-Glu)$_2$-Lys-(Glu-Phe)$_2$-Glu-Pro, (SEQ ID NO: 18)
Pro-Glu-(Phe-Glu)$_5$-(Gly)$_3$-Arg-Gly-Asp-Ser, (SEQ ID NO: 19)
(Phe-Glu)$_3$-Pro-(Gly)$_3$-Arg-Gly-Asp-Ser, (SEQ ID NO: 20)
Ac-Pro-Asp-(Phe-Asp)$_5$-Pro-NH$_2$, (SEQ ID NO: 21)
Pro-Asp-(Phe-Asp)$_6$, (SEQ ID NO: 22)
(Phe-Asp)$_6$, (SEQ ID NO: 23)
Pro-Glu-(Phe-Glu)$_5$-Pro, (SEQ ID NO: 24)
Pro-Asp-(Phe-Asp)$_5$-Pro-NH$_2$, (SEQ ID NO: 25)
(Phe-Glu)$_5$, (SEQ ID NO: 26)
(Phe-Glu)$_6$, (SEQ ID NO: 27)
(Phe-Glu)$_7$, (SEQ ID NO: 28)
Pro-Asp-(Phe-Asp)$_4$, (SEQ ID NO: 29)
Pro-Asp-(Phe-Asp)$_6$, (SEQ ID NO: 30)
Pro-Asp-(Phe-Asp)$_8$, (SEQ ID NO: 31)
(Phe-Asp)$_5$, (SEQ ID NO: 32)
(Phe-Asp)$_6$,

5

-continued (SEQ ID NO: 33)

(Phe-Asp)₇, (SEQ ID NO: 34)

Pro-Asp-(Phe-Asp)₅-Pro-Arg-Gly-Asp-Ser, (SEQ ID NO: 35)

Pro-(Phe-Asp)₃-Pro,
and (SEQ ID NO: 36)

Pro-(Phe-Asp)₃-Pro-(Gly)₃-Arg-Gly-Asp-Ser, or a salt thereof.

Each possibility represents a separate embodiment.

According to one embodiment, the peptide comprises Pro-(Asp-Phe)₅-Asp-Pro (SEQ ID NO: 1; designated herein "PFD5"). In another embodiment, the peptide comprises the sodium salt of a peptide having a sequence as set forth in SEQ ID NO:1 (designated herein "PFD5 sodium").

According to certain embodiments, the composition comprises from about 0.2% to about 20% w/v of the peptide or a salt thereof, including each value within the specified range. According to particular embodiments, the composition comprises from about 0.5% to about 10% w/v of the peptide or a salt thereof, including each value within the specified range. According to specific embodiments, the composition comprises from about 0.5% to about 5% w/v of the peptide or a salt thereof, including each value within the specified range.

According to some embodiments, the composition is formulated for topical administration. According to other embodiments, the composition is formulated for intradermal administration. According to yet other embodiments, the composition is formulated for subcutaneous administration.

According to various embodiments, the composition is in a form selected from the group consisting of a gel, a hydrogel, a lotion, a cream, a milk, an aerosol, a spray, a foam, a mousse, liquid drops, a liquid wash, an emulsion, and a suspension. Each possibility represents a separate embodiment. According to exemplary embodiments, the composition is in a form of a hydrogel.

According to particular embodiments, the dermatologically acceptable carrier comprises at least one of a thickener, a diluent, a moisturizer, an emulsifier, a humectant, a surfactant, a buffering or pH adjusting agent, a film forming agent, a foaming agent, an anti-foaming agent, a preservative, an anti-oxidant, a fragrance, a solvent, a propellant, a colorant, and a combination or mixture thereof. Each possibility represents a separate embodiment.

According to certain embodiments, the composition is useful as a dermal or soft tissue filler. According to particular embodiments, the present invention provides a method for dermal filling, the method comprising the step of locally administering to a subject in need thereof an effective amount of a dermatological composition as disclosed herein. According to one embodiment, the composition is administered into or under the skin at a site where dermal filling is desired.

According to other embodiments, the composition is useful in treating a soft tissue defect. According to particular embodiments, the present invention provides a method for treating a soft tissue defect, the method comprising the step of injecting or implanting to a subject in need thereof an effective amount of a dermatological composition as disclosed herein. According to various embodiments, treating a soft tissue defect comprises face or body contouring. According to further embodiments, treating a soft tissue defect comprises breast augmentation following mastectomy.

According to additional embodiments, the dermatological composition may further comprise a plurality of cells obtained from adipose tissue. According to certain embodiments, the plurality of cells obtained from adipose tissue comprise adipocytes and/or adipose-derived stem cells. According to some embodiments, the plurality of cells obtained from adipose tissue are autologous. According to particular embodiments, the autologous cells obtained from adipose tissue are obtained by lipoaspiration. According to other embodiments, the plurality of cells obtained from adipose tissue are allogeneic. According to further embodiments, the dermatological composition which further comprises a plurality of cells obtained from adipose tissue is useful for treating a soft tissue defect.

According to further embodiments, the dermatological composition may further comprise at least one of hyaluronic acid, collagen, gelatin, elastin, laminin, and fibronectin. Each possibility represents a separate embodiment.

According to some embodiments, the dermatological composition is useful for 3D bioprinting of an artificial tissue. In accordance with these embodiments, the present invention provides a method for 3D bioprinting of an artificial tissue, the method comprising the step of supplementing the dermatological composition as disclosed herein to a 3D bioprinter.

According to various embodiments, the present invention provides a pre-filled syringe comprising a dermatological composition as disclosed herein. According to some embodiments, the dermatological composition is sterile.

According to other embodiments, the composition is useful as a topical composition for treating a skin condition. According to various embodiments, the skin condition is selected from the group consisting of cuts, wounds, burns, insect bites, jellyfish stings, a rash, skin allergic responses, and skin lesions. Each possibility represents a separate embodiment. According to specific embodiments, the present invention provides a method for treating a skin condition selected from the group consisting of cuts, wounds, burns, insect bites, jellyfish stings, a rash, skin allergic responses, and skin lesions, the method comprising the step of topically administering to a subject in need thereof an effective amount of a dermatological composition as disclosed herein. Each possibility represents a separate embodiment.

According to additional embodiments, the composition is useful as a cosmetic composition. In accordance with these embodiments, the composition is useful in treating an epidermal condition related to aging selected from the group consisting of elastosis, atrophy of the skin, fine lines, wrinkles, enlarged pores, hyperpigmentation, hypopigmentation, sagging skin, rough skin, and dry skin. Each possibility represents a separate embodiment. According to further embodiments, the present invention provides a method for treating an epidermal condition related to aging selected from the group consisting of elastosis, atrophy of the skin, fine lines, wrinkles, enlarged pores, hyperpigmentation, hypopigmentation, sagging skin, rough skin, and dry skin, the method comprising the step of locally administering to a subject in need thereof an effective amount of a dermatological composition as disclosed herein. Each possibility represents a separate embodiment.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DETAILED DESCRIPTION OF THE INVENTION

Figure 1A:
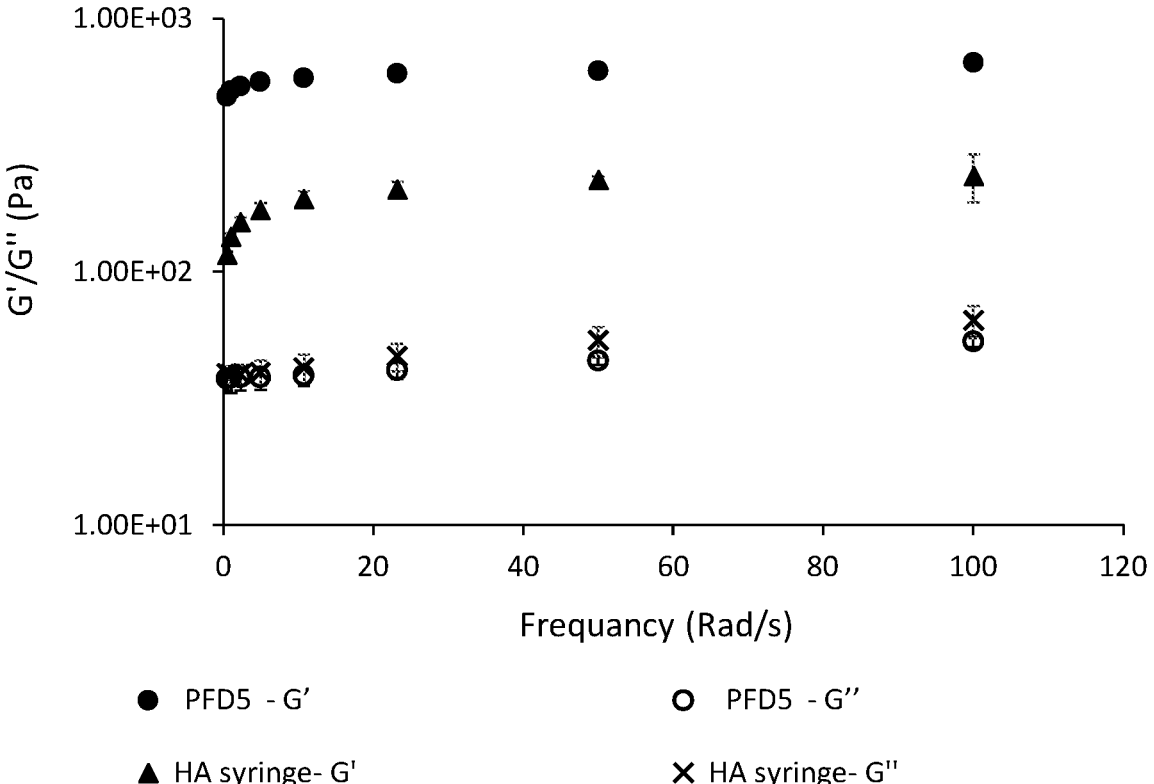
FIGS. 1A-1B. (1A) Elastic and loss moduli and (1B) Viscosity of a PFD5 2.5% w/v hydrogel according to certain embodiments of the present invention vs. a commercial hyaluronic acid, crosslinked, dermal filler (HA syringe) showing a higher G' of the PFD5 hydrogel.

The present invention relates to dermatological compositions comprising amphiphilic peptides and salts or derivatives thereof useful as dermal fillers or soft tissue fillers, and in treating, preventing, minimizing, diminishing or reversing various skin-related conditions.

The principles and operation of the present invention may be better understood with reference to the accompanying descriptions. Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

It is now disclosed for the first time that peptides comprising alternating hydrophobic/hydrophilic amino acid residues, in which the hydrophilic amino acid residues are predominantly acidic, can be used as dermal fillers for face and body contouring, correcting skin atrophy, improving the firmness or elasticity of skin and smoothing of fine-lines or wrinkles. The peptides can further be used to treat a variety of skin-related conditions including age-related conditions and trauma-induced skin disorders. Also encompassed by the present invention is the use of the peptides and compositions comprising said peptides for filling, augmentation and regeneration of soft tissue in a target region of a subject in need thereof and as components of bioink for 3D artificial tissue bioprinting.

According to certain aspects and embodiments, there is provided a dermatological composition comprising a peptide or derivatives or salts thereof comprising 1 to 20 pairs of hydrophobic-hydrophilic alternating amino acid residues, wherein the hydrophilic amino acid residue is selected from the group consisting of a negatively charged amino acid, a hydroxyl-containing amino acid, and a phosphorylated-hydroxyl-containing amino acid, and wherein said peptide has no more than 10% positively charged amino acid residues, and a dermatologically acceptable carrier.

As used herein, the term "dermatological composition" refers to formulations for use in aesthetics, plastic surgery, restorative surgery, tissue bulking, or in the field of cosmetics. Each possibility represents a separate embodiment. The term "dermatological composition" also refers to formulations that facilitate wound healing and tissue regeneration and/or serve as a scaffold to generate artificial tissues through proliferation of cells in culture. In certain embodiments, the compositions provide tissue augmentation, for example, as a biocompatible filler material, such as for face and body contouring or for augmenting a body cavity or void.

Typical peptides lengths within the scope of the present invention include, but are not limited to, 2 to 40 amino acids, including each integer within the specified range. In other embodiments, the length of the peptide is about 7 to about 28 amino acids, about 9 to about 20 amino acids, or about 11 to about 18 amino acids, including each integer within the specified ranges. For examples, the dermatological composition of the present invention encompasses peptides having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids, with each possibility representing a separate embodiment.

Also included within the scope of the present invention are salts and derivatives of the peptides used in the disclosed compositions and methods.

As used herein, the term "salts" refers to salts of carboxyl groups also termed base addition salts and to acid addition salts of amino or guanidino groups of the peptide molecule. Suitable base addition salts include, but are not limited to, metallic salts of calcium, lithium, magnesium, potassium, sodium, aluminum, ferric and zinc; ammonium salts derived from ammonia, primary, secondary, tertiary and quaternary amines, non-limiting examples of which are trimethylamine, cyclohexylamine, benzylamine, dibenzylamine, 2-hydroxyethylamine, bis(2-hydroxyethyl)amine, phenylethylbenzylamine, dibenzylethylenediamine, procaine, chloroprocaine, piperidine, monoethanolamine, triethanolamine, quinine, choline, N-methylglucosamine. Each possibility represents a separate embodiment. Salts with amino acids such as glycine, ornithine, histidine, phenylglycine, lysine, and arginine are contemplated. Each possibility represents a separate embodiment. Furthermore, any zwitterionic salt formed by a carboxylic acid and an amino or guanidino groups of the peptide molecule are contemplated as well.

Suitable acid addition salts include salts derived from inorganic acids such as, but not limited to, hydrochloric, nitric, phosphoric, sulfuric, hydrobromic, hydriodic, and the like, as well as salts derived from organic acids such as aliphatic mono- and dicarboxylic acids such as acetic acid or oxalic acid, phenyl-substituted alkanoic acids, hydroxy alkanoic acids, alkanedioic acids, aromatic acids, aliphatic and aromatic sulfonic acids and the like. Each possibility represents a separate embodiment. The salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Each possibility represents a separate embodiment. Also contemplated are salts of amino acids such as arginate and the like and gluconate or galacturonate. Each possibility represents a separate embodiment.

The acid addition salts may be prepared by known methods of the art in which the free base form is brought into contact with a sufficient amount of the desired acid to produce the salt. The base addition salts are prepared by known methods of the art in which the free acid form is brought into contact with a sufficient amount of the desired base to produce the salt.

"Derivatives" of the peptides of the invention as used herein cover derivatives which may be prepared from the functional groups which occur as side chains on the residues or the N- or C-terminal groups, by means known in the art, and are included in the invention provided that they do not adversely affect the benefits of the compositions containing them and do not confer toxic properties to said compositions.

These derivatives may include, for example, aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or aroyl groups), or O-acyl derivatives of free hydroxyl group (e.g., that of seryl or threonyl residues) formed by reaction with acyl moieties. Additional derivatives within the scope of the present invention include peptides formed by phosphorylation of hydroxyl-containing amino acids. It is contemplated that the amino acid residues of the present invention include both D- and L-amino acids, preferably L-amino acids.

As used herein, the term "a hydrophobic amino acid residue" refers to the following amino acids: Alanine (Ala; A), Isoleucine (Ile; I), Leucine (Leu; L), Phenylalanine (Phe; F), Valine (Val; V), and Tryptophan (Trp; W). Each possibility represents a separate embodiment. Currently preferred are Phenylalanine (Phe; F) and Leucine (Leu; L). Each possibility represents a separate embodiment.

As used herein, the term "a hydrophilic amino acid residue" refers to the following amino acids: Glutamic acid (Glu; E), Aspartic acid (Asp; D), Tyrosine (Tyr; Y), Serine (Ser; S), Threonine (Thr; T), Phosphoserine (Ser(PO$_4$); S(PO$_4$)), Phosphothreonine (Thr(PO$_4$); T(PO$_4$)), and Phosphotyrosine (Tyr(PO$_4$); Y(PO$_4$)). Each possibility represents a separate embodiment.

According to additional embodiments, the peptide further comprises at least one terminal Proline (Pro) residue. According to various embodiments, the peptide further comprises two terminal Pro residues.

According to certain aspects and embodiments, the peptide comprises an amino acid sequence represented by the following Formula I:

$$\text{X-(hydrophobic-hydrophilic)}_n\text{-B} \qquad \text{(Formula I)}$$

or a salt thereof, with the following designations:

n is an integer from 1 to 20, including each integer within the specified range;

hydrophobic is a hydrophobic amino acid residue as defined hereinabove;

hydrophilic is a hydrophilic amino acid residue as defined hereinabove;

X is Pro, Pro-hydrophilic or the peptide's amino terminus; and

B is Pro or the peptide's carboxy terminus.

In various aspects and embodiments, the peptide comprises a sequence comprising any of the following formulae X-(Phe-Glu)$_n$-B, X-(Phe-Asp)$_n$-B, X-(Leu-Glu)$_n$-B, and X-(Leu-Asp)$_n$-B or a salt thereof, wherein n, X, and B are as defined hereinabove. Each possibility represents a separate embodiment.

Non-limiting examples of peptides within the scope of the present invention are listed in Table 1 below:

TABLE 1

| SEQ ID NO: | Sequence |
|---|---|
| 1 | Pro-(Asp-Phe)$_5$-Asp-Pro |
| 2 | Pro-Glu-(Phe-Glu)$_5$ |
| 3 | Glu-(Phe-Glu)$_5$-Pro |
| 4 | Pro-(Ser-Phe)$_5$-Ser-Pro |
| 5 | Pro-(SerPO$_4$-Phe)$_5$-SerPO$_4$-Pro |
| 6 | Pro-(TyrPO$_4$-Phe)$_5$-TyrPO$_4$-Pro |
| 7 | Pro-(Glu-Leu)$_5$-Glu-Pro |
| 8 | Pro-(Asp-Leu)$_5$-Asp-Pro |
| 9 | Pro-(Ser-Leu)$_5$-Ser-Pro |
| 10 | Pro-(SerPO$_4$-Leu)$_5$-SerPO$_4$-Pro |
| 11 | Pro-(TyrPO$_4$-Leu)$_5$-TyrPO$_4$-Pro |
| 12 | Pro-(Glu-Phe-Ser-Phe)$_4$-Glu-Pro |
| 13 | Pro-(SerPO$_4$-Phe-Ser-Phe)$_4$-Ser-Pro |
| 14 | Pro-(SerPO$_4$-Phe-Glu-Phe)$_4$-Glu-Pro |
| 15 | Pro-(SerPO$_4$-Phe-Asp-Phe)$_4$-Asp-Pro |
| 16 | Ala-Leu-Glu-(Phe-Glu)$_3$-Pro-Ala-(Glu-Phe)$_3$-Glu-Leu-Pro-Ala-Leu-Glu-(Phe-Glu)$_3$-Pro |
| 17 | Pro-Glu-(Phe-Glu)$_2$-Lys-(Glu-Phe)$_2$-Glu-Pro |
| 18 | Pro-Glu-(Phe-Glu)$_5$-(Gly)$_3$-Arg-Gly-Asp-Ser |
| 19 | (Phe-Glu)$_3$-Pro-(Gly)$_3$-Arg-Gly-Asp-Ser |
| 20 | Ac-Pro-Asp-(Phe-Asp)$_5$-Pro-NH$_2$ |
| 21 | Pro-Asp-(Phe-Asp)$_6$ |
| 22 | (Phe-Asp)$_6$ |
| 23 | Pro-Glu-(Phe-Glu)$_5$-Pro |
| 24 | Pro-Asp-(Phe-Asp)$_5$-Pro-NH$_2$ |
| 25 | (Phe-Glu)$_5$ |
| 26 | (Phe-Glu)$_6$ |
| 27 | (Phe-Glu)$_7$ |

TABLE 1-continued

| SEQ ID NO: | Sequence |
|---|---|
| 28 | Pro-Asp-(Phe-Asp)$_4$ |
| 29 | Pro-Asp-(Phe-Asp)$_6$ |
| 30 | Pro-Asp-(Phe-Asp)$_8$ |
| 31 | (Phe-Asp)$_5$ |
| 32 | (Phe-Asp)$_6$ |
| 33 | (Phe-Asp)$_7$ |
| 34 | Pro-Asp-(Phe-Asp)$_5$-Pro-Arg-Gly-Asp-Ser |
| 35 | Pro-(Phe-Asp)$_3$-Pro |
| 36 | Pro-(Phe-Asp)$_3$-Pro-(Gly)$_3$-Arg-Gly-Asp-Ser |

The peptides, derivatives and salts used in the compositions and methods of the present invention may be synthesized using any method known in the art including, but not limited to, solid phase and liquid phase peptide synthesis. In some embodiments, the peptides, are synthesized using conventional synthesis techniques, e.g., by chemical synthesis techniques. These methods include exclusive solid phase synthesis, partial solid phase synthesis methods, fragment condensation, and classical solution synthesis. Solid phase peptide synthesis procedures are well known in the art and described for example by Stewart & Young, Solid Phase Peptide Syntheses, Pierce Chemical Company, 1984, 2nd Ed. A skilled artesian may synthesize any of the peptides of the present invention by using an automated peptide synthesizer using standard chemistry such as, for example, t-Boc or Fmoc chemistry. Synthetic peptides can be purified by preparative high-performance liquid chromatography (HPLC) as known in the art and the sequence of which can be confirmed via amino acid sequencing.

Alternatively, the peptides may be prepared by known recombinant DNA techniques by cloning and expressing within a host microorganism or cell a DNA fragment carrying a coding sequence of the selected peptide or construct. Such techniques were described for example, by Bitter et al. Met. Enzymol. 1987, 153:516-544; Studier et al. Met. Enzymol. 1990, 185:60-89; Brisson et al. Nature, 1984, 310:511-514; Takamatsu et al. EMBO J. 1987, 6:307-311; Coruzzi et al. EMBO J. 1984, 3:1671-1680; Brogli et al. Sci. 1984, 224:838-843, Gurley et al. Mol. Cell. Biol. 1986, 6:559-565; and Weissbach & Weissbach, Met. Plant Mol. Biol. 1988, Academic Press, NY, VIII: 421-463. Coding sequences for the peptides can be prepared synthetically, or can be derived from viral RNA by known techniques, or from available cDNA-containing plasmids.

In some aspects and embodiments, the peptide of the invention is present in the composition in an amount of from about 0.2% to about 20% (w/v) of the total weight of the composition, including each value within the specified range. Typically, the amount of the peptide in the composition is in the range of about 0.5% to about 10% (w/v) of the total weight of the composition, including each value within the specified range. In certain embodiments, the amount of the peptide in the composition is in the range of about 0.5% to about 5% (w/v) of the total weight of the composition, including each value within the specified range. For example, the amount of the peptide in the composition is about 0.2%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (w/v) of the total weight of the composition, with each possibility representing a separate embodiment.

According to the principles of the present invention the peptides are admixed with one or more chemical components such as dermatologically acceptable carriers designed to facilitate administration of a compound to a subject, preferably a human subject. The term "dermatologically acceptable carrier" as used herein refers to an excipient that is biocompatible and does not cause significant irritation to the skin or abrogate the beneficial activity and properties of the peptide of the present invention. Suitable dermatologically acceptable carriers within the scope of the present invention include, but are not limited to, a thickener, a diluent, a moisturizer, an emulsifier, a humectant, a surfactant, a buffering or pH adjusting agent, a film forming agent, a foaming agent, an anti-foaming agent, a preservative, an anti-oxidant, a fragrance, a solvent, a propellant, a colorant, and a combination or mixture thereof. Each possibility represents a separate embodiment.

Suitable thickeners include, but are not limited to, fatty acids and alcohols such as stearic acid and stearyl alcohol; gums such as xanthan, carrageenan, gelatin, cellulose gum, agarose, karaya, pectin, amylopectin, and locust beans gum; and various polymers such as hydroxypropyl methylcellulose (HPMC), hydroxypropyl cellulose (HPC), hydroxymethyl cellulose, hydroxyethyl cellulose, methyl cellulose, carboxymethyl cellulose, polyvinylpyrrolidone (povidone, PVP), polyvinyl alcohol, medium to high molecular weight polyethylene glycols (PEG-3350, PEG-6000, etc.), glucosides, tetrasodium etidronate, polyacrylic acid, polymethacrylic acid, acrylamides copolymer, sodium acrylates copolymer, sodium alginate, calcium alginate, magnesium alginate, alginic acid, hyaluronic acid, polyglucuronic acid (poly-α- and -β-1,4-glucuronic acid), chondroitin sulfate, furcellaran, polycarboxylic acids, carbomer, bentonite, chitin, chitosan, carboxymethyl chitin, and crosslinked polyacrylate materials available under the trademark Carbopol®. Each possibility represents a separate embodiment. In one embodiment, the composition comprises from about 0.5% to about 50% w/w of a thickener, including each value within the specified range.

Suitable diluents include, but are not limited to, minerals such as hydroxyapatite, calcium phosphate, calcium carbonate, calcium gluconate, calcium oxalate, calcium sulfate, calcium chloride, magnesium phosphate, magnesium carbonate, magnesium gluconate, magnesium oxalate, magnesium sulfate, magnesium chloride, zinc phosphate, zinc carbonate, zinc gluconate, zinc oxalate, zinc sulfate, zinc chloride, sodium bicarbonate, mica, talc, kaolin, silicon dioxide (e.g. silica), and a mixture or combination thereof. Each possibility represents a separate embodiment. Additional diluents include, but are not limited to, biodegradable or non-biodegradable polymers such as nylon, polyethylene, polymethacrylate, Teflon, poly (D,L-lactide-co-glycolide) (PLGA), poly (D,L-lactide) (PLA), polyglycolides (PGA), polycaprolactone, polyhydroxybutyrate, polyorthoesters, polyalkaneanhydrides, polyester anhydrides, gelatin, collagen, cellulose, polyphosphazene and a mixture or combination thereof. Each possibility represents a separate embodiment. Further diluents within the scope of the present invention include, but are not limited to, various sugars and types of starch, polysugars, dextrin, cyclodextrins (e.g. β-CD, hydroxypropyl-β-CD, sulfobutylether-CD), microcrystalline cellulose, and a mixture or combination thereof. Each possibility represents a separate embodiment. In one embodiment, the composition comprises from about 0.5% to about 50% w/w of a diluent, including each value within the specified range.

Suitable moisturizers include, but are not limited to, glycerin, hydrocarbon oils and waxes, including mineral oil, petrolatum, paraffin, ceresin, ozokerite, microcrystalline wax, polyethylene, and perhydrosqualene; silicone oils; triglyceride fats and oils, including those derived from vegetable, animal and marine source including jojoba oil and shea butter; acetoglyceride esters, such as acetylated monoglycerides; ethoxylated glycerides, such as ethoxylated glyceryl monostearate; fatty acids, fatty alcohols and derivatives thereof. Each possibility represents a separate embodiment. Other suitable emollients include, but are not limited to, caprylic or capric triglyceride; lanolin and lanolin derivatives; polyhydric alcohols and polyether derivatives; polyhydric alcohol esters; wax esters; vegetable waxes; phospholipids, such as lecithin and derivatives; sterols, including, but not limited to, cholesterol and cholesterol fatty acid esters; amides, such as fatty acid amides, ethoxylated fatty acid amides, and solid fatty acid alkanolamides. Each possibility represents a separate embodiment. In one embodiment, the composition comprises from about 0% to about 10% w/w of a moisturizer, including each value within the specified range.

Suitable emulsifiers include, but are not limited to, polyethylene glycol ethers of stearic acid such as steareth-2, steareth-4, steareth-6, steareth-7, steareth-10, steareth-11, steareth-13, steareth-15, and steareth-20, glyceryl stearate, stearyl alcohol, cetyl alcohol, cetearyl alcohol, behenyl alcohol, diethanolamine, lecithin, and polyethylene glycols. Each possibility represents a separate embodiment. In one embodiment, the composition comprises from about 0% to about 10% w/w of an emulsifier, including each value within the specified range. In another embodiment, the composition comprises from about 0% to about 5% w/w of an emulsifier, including each value within the specified range.

Suitable humectants include, but are not limited to, glycols such as triethylene glycol, tripropylene glycol, propylene glycol, polypropylene glycols, butylene glycol, polyethylene glycols, sugar alcohols such as sorbitol, hexylene, urea, and collagen. Each possibility represents a separate embodiment. In one embodiment, the composition comprises from about 0% to about 5% w/w of a humectant, including each value within the specified range.

Suitable surfactants are cationic, anionic or zwitterionic including, but not limited to, polyoxyethylene glycol octylphenol ethers, polyoxyethylene glycol alkylphenol ethers, polyoxyethylene glycol sorbitan alkyl esters (polysorbate 60, polysorbate 80, etc.), sorbitan alkyl esters, block copolymers of polyethylene glycol and polypropylene glycol (poloxamer), polyethyleneglycol-tocopheryl succinate, DL a tocopheryl acetate, polyethoxylated castor oil derivatives (cremophor EL. Cremophor RH40), dioctyl sodium sulfosuccinate, perfluorooctanesulfonate, alkylbenzene sulfonates, sodium lauryl ether sulfate, ammonium laureth sulfate, ammonium lauryl sulfate, disodium laureth sulfosuccinate, lignosulfonate, sodium stearate, benzalkonium chloride, cetylpyridinium chloride, benzethonium chloride, cetyl trimethylammonium bromide, cetyl trimethylammonium chloride, and betaines. Each possibility represents a separate embodiment. In one embodiment, the composition comprises from about 0% to about 30% w/w of a surfactant, including each value within the specified range. In another embodiment, the composition comprises from about 0% to about 20% w/w of a surfactant, including each value within the specified range. In yet another embodiment, the composition comprises from about 0% to about 5% w/w of a surfactant, including each value within the specified range.

Suitable buffering or pH adjusting agents include, but are not limited to, acidic buffering or pH adjusting agents such as short chain fatty acids, citric acid, acetic acid, hydrochloric acid, sulfuric acid and fumaric acid; and basic buffering or pH adjusting agents such as tris, HEPES, Hanks' Balanced Salt Solution (HBSS), sodium carbonate, sodium bicarbonate, sodium hydroxide, potassium hydroxide, and magnesium hydroxide. Each possibility represents a separate embodiment. In one embodiment, the composition comprises from about 0% to about 10% w/w of a buffering or pH adjusting agent, including each value within the specified range. In another embodiment, the composition comprises from about 0% to about 5% w/w of a buffering or pH adjusting agent, including each value within the specified range. In yet another embodiment, the composition comprises from about 0% to about 1% w/w of a buffering or pH adjusting agent, including each value within the specified range. In certain embodiments, the composition has a pH in the range of about 4 to about 8, including each value within the specified range. In other embodiments, the composition has a pH in the range of about 5 to about 7, including each value within the specified range. Typical pH values of the composition include, but are not limited to, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. Each possibility represents a separate embodiment.

Suitable film forming agents include, but are not limited to, polyvinylpyrrolidone, acrylates, acrylamides, methacrylates, shellac, acacia, and hydroxyethylcellulose. Each possibility represents a separate embodiment. In one embodiment, the composition comprises from about 0% to about 20% w/w of a film forming agent, including each value within the specified range.

Suitable foaming agents include, but are not limited to, isopropyl myristate, oxyalkylated sulfates and ethoxylated alcohol sulfates. Each possibility represents a separate embodiment. In one embodiment, the composition comprises from about 0% to about 10% w/w of a foaming agent, including each value within the specified range.

Suitable anti-foaming agents include, but are not limited to, simethicone, and sorbitan sesquoleate. Each possibility represents a separate embodiment. In one embodiment, the composition comprises from about 0% to about 10% w/w of an anti-foaming agent, including each value within the specified range.

Suitable preservatives include, but are not limited to, methylparaben, propylparaben, butylparaben, ethylparaben, potassium sorbate, trisodium EDTA, tetrasodium EDT, edetate disodium, benzophenone, 2-bromo-2-nitropane-1,3-diol, butylated hydroxytoluene, digluconate, citric DMDM acid, hydantoin, formaldehyde, chlorhexidine methylchloroisothiazolinone, methylisothiazolinone, methyldibromo glutaronitrile, sodium benzoate, phenoxyethanol, ethyl alcohol, benzyl alcohol, diazolidinyl urea, imidazolidinyl urea, and quaternium-15. Each possibility represents a separate embodiment. In one embodiment, the composition comprises from about 0% to about 5% w/w of a preservative, including each value within the specified range.

Suitable anti-oxidants include, but are not limited to, ascorbic acid, ubiquinone, tocophenyl acetate, N-acetyl cysteine (NAC) or a derivative thereof, and sodium bisulfite. Each possibility represents a separate embodiment. In one embodiment, the composition comprises from about 0% to about 10% w/w of an anti-oxidant, including each value within the specified range.

Suitable fragrances include, but are not limited to, chamomile oil, lavender oil, and various plant extracts such as *camellia sinesis*. Each possibility represents a separate embodiment. In one embodiment, the composition comprises from about 0% to about 5% w/w of a fragrance, including each value within the specified range.

Suitable solvents include, but are not limited to, water, lower alcohols such as ethanol and isopropanol, propylene glycol, ammonium xylenesulfonate, and low molecular weight polyethylene glycols such as, e.g. PEG-300, PEG-1450 etc. Each possibility represents a separate embodiment. In one embodiment, the composition comprises from about 0% to about 99% w/w of a solvent, including each value within the specified range. In another embodiment, the composition comprises from about 10% to about 90% w/w of a solvent, including each value within the specified range. In yet another embodiment, the composition comprises from about 20% to about 80% w/w of a solvent, including each value within the specified range.

Suitable propellants include, but are not limited to, hydrocarbons having 4 to 7 carbon atoms such as isopentane. Additional propellants include, but are not limited to, chlorinated, fluorinated and chlorofluorinated lower molecular weight hydrocarbons as well as nitrous oxide, carbon dioxide, butane, and propane. Each possibility represents a separate embodiment. The propellants may be used in a quantity and under a pressure suitable to provide proper release of the peptide from the container at the appropriate amount.

Suitable colorants include, but are not limited to, alumina (dried aluminum hydroxide), annatto extract, calcium carbonate, canthaxanthin, caramel, β-carotene, cochincal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, disodium dityrylbiphenyl, mica, dentifrices, talc, titanium dioxide, aluminum powder, bronze powder, copper powder, and zinc oxide or a mixture or combination thereof. Each possibility represents a separate embodiment. In one embodiment, the composition comprises from about 0% to about 5% w/w of a colorant, including each value within the specified range.

Additional ingredients that may be included in the compositions of the present invention are sunscreens and tanning agents. Sunscreens include those materials commonly employed to block UV light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are also known as parsol MCX and benzophenone-3, respectively. If present in the composition, the amount of sunscreen employed can vary depending upon the desired degree of protection from UV radiation. The sunscreen must be compatible with the active compound but in general the composition may comprise from about 0.5% to about 20% w/w of a sunscreen, including each value within the specified range. Exact amounts will vary depending upon the sunscreen chosen and the desired Sun Protection Factor (SPF).

Further ingredients that may be included in the compositions of the present invention are vitamins and vitamin derivatives such as, for example vitamin A, vitamin B, vitamin C, vitamin D, vitamin E, vitamin K and derivatives thereof including, for example, a tocopherol; and various plant extracts such as, for example *Aloe vera, Aloe barbadensis,* castor oil, *Citrus limonium, Citrus paradisi, Citrus sinensis, Elaesis guineensis,* etc. Each possibility represents a separate embodiment. Additionally, depigmenting agents that suppress melanocyte metabolic processes of the skin and inhibit the enzymatic oxidation of tyrosine to DOPA (3, 4-dihydroxyphenylalanine) may also be incorporated into the compositions of the present invention. Further ingredients that may be included in the compositions of the present invention are botulinum toxins of type A, B, C, D, E, F, G, and mixtures thereof, with each possibility representing a separate embodiment.

Further included within the scope of the present invention is the incorporation of a component comprising hyaluronic acid, collagen, gelatin, elastin, laminin, fibronectin or a mixture or combination thereof in the compositions disclosed herein. When incorporated as part of the composition, the weight ratio between the peptide of the invention and the component typically ranges from about 100:1 to about 1:100, including all iterations of ratios within the specified range. In one aspect and embodiment, hyaluronic acid and derivatives thereof are incorporated in the composition. The hyaluronic acid and derivatives at different chain lengths may be admixed with the peptides and dermatologically acceptable carriers and/or they may be conjugated to the peptides disclosed herein. Each possibility represents a separate embodiment. In some embodiments, the benefit obtained by using a composition comprising a mixture or combination of hyaluronic acid and the peptides disclosed herein is synergistic. If incorporated into the composition, the hyaluronic acid may be a high molecular weight hyaluronic acid having a molecular weight in the range of about 1.0 million Daltons (MDa) to about 4.0 MDa or a low molecular weight hyaluronic acid having a molecular weight in the range of about 1,000 Da to about 1.0 MDa, including each value within the specified ranges. The hyaluronic acid may be uncrosslinked or crosslinked to various degrees with a crosslinking agent such as, but not limited to, 1,4-butanediol diglycidyl ether (BDDE), 1,4-bis(2,3-epoxypropoxy)

butane, 1,4-bisglycidyloxybutane, 1,2-bis(2,3-epoxy-propoxy)ethylene, 1-(2,3-epoxypropyl)-2,3-epoxycyclohexane, and 1,4-butanediol diglycidyl ether. Each possibility represents a separate embodiment.

According to the principles of the present invention, the compositions disclosed herein may further comprise a local anesthetic (LA), e.g. lidocaine, in order to ameliorate any pain sensation during and/or after administration. Although the composition of the present invention can be administered via injection through a 30 gauge needle or less, it may be advantageous to add a local anesthetic to the formulation to improve compliance. When added, the concentration of the local anesthetic is typically less than 10% w/v, for example about 0.01% w/v to 10% w/v, including each value within the specified range. Exemplary concentrations include about 0.05% w/v to about 5% w/v, about 0.1% w/v to about 1% w/v, etc.

Further included within the scope of the present invention is the incorporation of cells obtained from adipose tissue in the compositions. According to one embodiment, the cells are adipocytes. According to another embodiment, the cells are adipose-derived stem cells. The compositions supplemented with adipose-derived cells may be used in adipose tissue reconstruction procedures for treating a soft tissue defect including, but not limited to, in subjects with inborn defects, trauma, or surgical resections. Each possibility represents a separate embodiment.

The hitherto adipose tissue reconstruction methods are either performed by applying harvested autologous tissue with its blood supply or by transferring autologous harvested fat. These methods rarely result in sufficient tissue augmentation due to delayed neovascularization associated with subsequent cell necrosis, fibrosis and graft volume shrinkage. Moreover, survival of the transplanted fat is very unpredictable with resorption generally occurring within 4-6 months after lipofilling.

The peptides of the present invention were shown to support the viability of adipocytes and can therefore be used in soft tissue augmentation procedures. Without being bound by any theory or mechanism of action, the peptides are capable of forming a semi-solid substrate for adipocytes attachment, enhances collagen formation that may further support adipocytes viability, and enhanced neo-vasculature.

The adipocytes or adipose-derived stem cells to be incorporated into the compositions may be obtained from any source. According to some embodiments, the cells are derived from human subcutaneous fat. According to particular embodiments, the cells are derived from human subcutaneous fat obtained by liposuction aspiration. The cells may be obtained by liposuction procedures in various areas of the body including stomach, hips, thighs, arms, neck and buttocks. Each possibility represents a separate embodiment. Any procedure of liposuction may be used according to the present invention for obtaining adipocytes or adipose-derived stem cells including, but not limited to, laser, ultrasound and fat removal by abdominoplasty, as known in the art.

The adipose tissue is processed to isolate the adipocytes or adipose-derived stem cells which are then harvested by methods known in the art. According to some embodiments, the adipocytes or adipose-derived stem cells are autologous. According to other embodiments, the adipocytes or adipose-derived stem cells are allogeneic. While the ratio of peptides to cells may vary, typically adipocytes or adipose-derived stem cells are mixed with the hydrogel compositions according to certain embodiments of the present invention in volume ratios of 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5, with each possibility representing a separate embodiment. Although the cells obtained from adipose tissue may be incorporated into a single composition with the peptides disclosed herein, it is to be understood that separate compositions are also contemplated by the present invention. Thus, according to certain embodiments, the present invention provides the co-administration of a dermatological composition comprising the amphiphilic peptide comprising alternating hydrophobic/hydrophilic amino acid residues and a composition comprising a plurality of cells obtained from adipose tissue.

The compositions of the present invention may be manufactured by processes well known in the art, e.g., by means of conventional mixing, dissolving, suspending, solubilizing, granulating, levigating, emulsifying, encapsulating, entrapping, spray-drying, or lyophilizing processes. They may be formulated in a conventional manner using one or more dermatologically acceptable carriers as described above, which facilitate processing of the peptides and peptide derivatives and salts into preparations which can be used dermatologically. After their manufacture, the compositions can be packaged and sterilized using e.g. filtration, steam autoclaving, ethylene oxide, γ-radiation, electron beam irradiation or other biocompatible methods. Autoclaving can be carried out using any suitable temperature, pressure and time. For example, a temperature of 80-120° C. for 20 minutes is suitable for many preparations. Irradiation can be performed with intensity in the range of about 10 to 50 kGy, or about 1 to 10 megaRad (MRad), including each value within the specified ranges.

Proper formulation is dependent upon the route of administration chosen. In particular, when the compositions are designed for soft tissue filling, intradermal administration and/or subcutaneous administration are contemplated. Each possibility represents a separate embodiment. In one embodiment, the administration is supra-periosteal. In other aspects and embodiments, when the compositions are designed for wound healing and for the treatment of various skin conditions or cosmetic uses, the compositions of the present invention are formulated for topical administration.

For topical, intradermal or subcutaneous administration, the compositions of the present invention may be formulated as a gel, a hydrogel, a lotion, a cream, a milk, an aerosol, a spray, a foam, a mousse, liquid drops, a liquid wash, an emulsion or a suspension. Each possibility represents a separate embodiment. Currently preferred for intradermal or subcutaneous administrations are compositions formulated as a hydrogel. The term "hydrogel" according to the present invention refers to a three-dimensional hydrated assembly of bioactive nanofibers. This definition includes dry "hydrogel forming peptides" that will swell in aqueous environments, as well as water-swollen materials. Typically, in hydrated hydrogels, according to the principles of the present invention, the amount of water in the compositions containing hydrogels ranges from about 1% to about 99% (w/v) of the total weight of the composition, including each value within the specified range. Exemplary ranges of water content include, but are not limited to, about 5% to about 20%, about 10% to about 40%, about 50% to about 70%, about 75% to about 95%, about 80% to about 99% (w/v) of the total weight of the composition, including each value within the specified ranges. A hydrogel according to the present invention can be tailored to possess a range of properties depending on the peptides of which the hydrogel is composed of and on additional materials that may be added thereto. Alternative forms of the compositions of the present invention may also be used including forms which are designed for reconstitution with a suitable vehicle prior to use. Intradermal delivery of the peptides, peptide derivatives or salts thereof through nanoneedles or microneedles for example using a patch as described in Larraneta et al. (Mater. Sci. Eng. R 104: 1-32, 2016) is also contemplated within the scope of the present invention.

In some aspects and embodiments, the dermatological composition disclosed herein exhibits elastic and loss moduli in the range of about 20 to about 5,000 Pa, for example about 100 to about 1,000 Pa, about 100 to about 1,500 Pa, about 100 to about 2,000 Pa, or about 100 to about 3,000 Pa, including each value within the specified ranges. Exemplary elastic and loss moduli include, but are not limited to, about 20, about 50, about 100, about 150, about 200, about 250, about 300, about 350, about 400, about 450, about 500, about 550, about 600, about 650, about 700, about 750, about 800, about 850, about 900, about 950, about 1,000, about 1,100, about 1,200, about 1,300, about 1,400, about 1,500, about 1,600, about 1,700, about 1,800, about 1,900, about 2,000, about 2,500, about 3,000, about 3,500, about 4,000, about 4,500, or about 5,000 Pa, with each possibility representing a separate embodiment.

In some aspects and embodiments, the dermatological composition disclosed herein exhibits a viscosity in the range of about 1 to about 5,000 Pas, for example about 10 to about 4,000 Pa*s, about 10 to about 2,500 Pa*s, or about 10 to about 1,000 Pa*s, including each value within the specified ranges. Exemplary viscosities include, but are not limited to, about 1, about 10, about 20, about 50, about 100, about 150, about 200, about 250, about 300, about 350, about 400, about 450, about 500, about 550, about 600, about 650, about 700, about 750, about 800, about 850, about 900, about 950, about 1,000, about 1,100, about 1,200, about 1,300, about 1,400, about 1,500, about 1,600, about 1,700, about 1,800, about 1,900, about 2,000, about 2,500, about 3,000, about 3,500, about 4,000, about 4,500, or about 5,000 Pa*s, with each possibility representing a separate embodiment.

In some aspects and embodiments, the dermatological composition disclosed herein swells upon imbibition of an aqueous medium by less than 100% of its initial volume, for example less than 80%, less than 70%, less than 60%, or less than 50% of its initial volume, with each possibility representing a separate embodiment. The dermatological composition of the present invention is contemplated to have sufficient cohesivity such that it remains localized in the site of administration.

The compositions of the present invention are useful as dermal fillers. Thus, there is provided a method for dermal filling, the method comprising the step of locally administering to a subject in need thereof an effective amount of a dermatological composition as disclosed herein. Dermal fillers can be used to treat moderate to severe facial wrinkles and folds such as nasolabial folds (i.e. that extend from the nose to the corners of the mouth). In one embodiment, a dermal filler can be a gel implant composition, preferably a hydrogel implant composition, that can be injected with a syringe into the mid to deep dermis in an area of choice (e.g. face). The dermis is the subsurface skin layer that contains connective tissue, nerve endings, and blood vessels. The compositions, when administered as dermal fillers can improve skin appearance by lifting and adding volume to the wrinkles and folds in the treatment area thereby inducing soft tissue augmentation. Further, in certain embodiments, improvement can be seen due to increased collagen production that results from administration of the composition.

The compositions of the present invention are useful as soft tissue fillers for treating a soft tissue defect in the face or body of a subject in need thereof. Thus, there is provided the use of the peptides disclosed herein for the preparation of a dermatological composition for treating a soft tissue defect. The dermatological composition is implanted or injected to the site of choice. Exemplary soft tissue defects that are treated by the dermatological compositions of the present invention include, but are not limited to, breast imperfections during breast reconstruction procedures, for example following mastectomy. In some aspects and embodiments, the compositions are used for face and body contouring.

Within the scope of the present invention are pre-filled syringes containing the dermatological compositions disclosed herein. Syringes suitable for use according to the present invention include, but are not limited to, those that have an internal volume of about 0.1 to about 5 ml that are equipped with needles or cannula having gauges of between about 18 G and about 40 G, including each value within the specified range. According to some embodiments, 25 G to 31G needles are desirable for minimal injection site damage. The compositions are sterilized prior to being inserted into the syringe or syringes already incorporated with the compositions are sterilized.

In some aspects and embodiments, the dermatological compositions disclosed herein can be injected with an extrusion force of less than 50 N, for example in the range of about 1 to about 50 N, about 1 to about 30 N, or about 1 to about 15 N, including each value within the specified ranges. Exemplary extrusion forces include, but are not limited to, about 1, about 2, about 3, about 4, about 5, about 6, about 7, about 8, about 9, about 10, about 15, about 20, about 25, about 30, about 35, about 40, about 45, or about 50 N injected through a 27-30 gauge needle. Each possibility represents a separate embodiment.

Within the scope of the present invention is the use of the dermatological compositions disclosed herein as components of bioink for 3D bioprinting of an artificial tissue. Bioprinting is a process by which an artificial tissue is generated using a bioink composed of cultured cells and a material that forms a supporting structure for the cells. The bioink is supplemented into a bioprinter to create 3D artificial tissues that can be used for regenerative medicine.

The compositions of the present invention are further useful in treating various skin conditions upon topical administration. Within the scope of the present invention is the treatment of cuts, wounds, burns, insect bites, jellyfish stings, a rash, skin allergic responses, and/or skin lesions. Each possibility represents a separate embodiment. Thus, there is provided the use of the peptides disclosed herein for the preparation of a dermatological composition for treating a skin condition selected from cuts, wounds, burns, insect bites, jellyfish stings, a rash, skin allergic responses, and skin lesions. In some embodiments, there is provided a method of treating a skin condition selected from the group consisting of cuts, wounds, burns, insect bites, jellyfish stings, a rash, skin allergic responses, and skin lesions, the method comprising the step of administering to a subject in need thereof an effective amount of a dermatological composition as disclosed herein.

The term "treating" as used herein refers to administering a therapeutic substance (i.e. the peptides, derivatives or salts of the present invention or compositions comprising same) effective to ameliorate, minimize, diminish or reverse a condition or symptoms associated therewith. The term "treating" as used herein also encompasses the prevention of symptoms of the skin conditions.

An "effective amount" as used herein is an amount of active ingredient capable of bringing about the desired effect, i.e. dermal filling or treatment of the skin condition. This amount depends on a number of parameters such as the exact composition that is used, the area of administration, the skin condition and the like. Compositions suitable for use in the context of the present invention include compositions wherein the peptide, derivative or salt of the invention is contained in an amount effective to achieve the intended purpose. Determination of an effective amount is well within the capability of those skilled in the art, especially in light of the detailed disclosure provided herein. For any preparation used in the methods of the invention, the effective amount can be estimated initially from in vitro and cell culture assays as described in e.g. Nakamura et al. (Exper. Derma. 27:495-500, 2018). For example, a certain dose can be formulated in an animal model to achieve a desired concentration or titer. Such information can be used to more accurately determine useful doses in humans. The dosage may vary depending upon the dosage form employed and the route of administration utilized. The exact formulation, route of administration and dosage can be chosen in view of the subject's condition. Although the compositions of the present invention may be administered at a single dose, multiple administrations at certain intervals are contemplated within the scope of the present invention. These may be adjusted according to individual characteristics and route of administration depending on the severity and responsiveness of the epidermal condition. The duration of treatment may last from several days to several weeks, months or years as desired. Typical dosages of the peptide, derivative or salt encompassed by the present invention include, but are not limited to, about 0.01 to about 1,000 mg/kg of body weight, about 0.1 mg/kg to about 100 mg/kg, about 1 mg/kg to about 100 mg/kg, about 10 mg/kg to about 75 mg/kg, about 0.1 mg/kg to about 1 mg/kg etc., including each value within the specified ranges. Exemplary non-limiting amounts include about 0.1 mg/kg, about 0.2 mg/kg, about 0.5 mg/kg, about 1 mg/kg, about 5 mg/kg, about 10 mg/kg, about 20 mg/kg, about 50 mg/kg, about 60 mg/kg, about 75 mg/kg, about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1,000 mg/kg. Each possibility represents a separate embodiment. Alternatively, the amount administered can be measured and expressed as molarity of the administered peptide, derivative or salt. By way of illustration and not limitation, the peptide, derivative or salt can be administered in a range of about 0.1 to about 100 mM, including each value within the specified range e.g., about 0.1. about 0.25, about 0.5, about 1 about 2, about 3, about 4, about 5, about 6, about 7, about 8, about 9, about 10, about 20, about 30, about 40, about 50, about 60, about 70, about 80, about 90 or about 100 mM. Each possibility represents a separate embodiment. Alternatively, the amount administered can be measured and expressed as mg/ml, µg/ml, or ng/ml.

As used herein, the term "administering" refers to bringing in contact with the peptide, derivative or salt of the present invention or a composition comprising same. Typically, administration can be accomplished by topically applying an effective amount of the composition to a region of the skin which exhibits an epidermal condition to be treated. As used herein "topical administration" also refers to administration that is accomplished by intradermal or subcutaneous injection of an effective amount of the composition to a region of the skin which exhibits an epidermal condition to be treated. Administration can be accomplished to living organisms, for example humans.

For soft tissue repair and regeneration, the compositions of the invention may further comprise at least one additional bioactive agent, such as a cytokine, a growth factor and their activators, platelets, etc. Each possibility represents a separate embodiment. Without wishing to be bound by theory, incorporation of such agent(s) into the composition of the present invention is contemplated to improve the efficacy of the compositions disclosed herein. For example, fibroblast growth factors and their variants, including FGF2, FGF4, FGF9 and FGF18, nerve growth factor genes (NGF) and certain FGFs for nerve healing, and general growth factors such as platelet-derived growth factor (PDGF), vascular endothelial growth factor (VEGF), insulin-like growth factor (IGF-1), keratinocyte growth factor (KGF), endothelial derived growth supplement (EDGF), epidermal growth factor (EGF) and other proteins may enhance the action of the dermatological compositions by releasing into the surrounding milieu active ingredients which facilitate the sequence of wound repair, enhance angiogenesis, and alter the rate of proliferation of cells. Other biologically active agents that may be incorporated into the compositions include analgesics, anti-inflammatory agents, anti-microbials, and enzymes. Each possibility represents a separate embodiment.

The compositions of the present invention are further useful for cosmetic uses, for example in treating an epidermal condition related to aging. Thus, there is provided the use of the peptides disclosed herein for the preparation of a dermatological composition for treating an epidermal condition related to aging. As used herein, the term "an epidermal condition related to aging" refers to age-related elastosis, atrophy of the skin, fine lines or wrinkles, skin imperfections, enlarged pores, spots including lentigines or solar lentigines, uneven skin tone or texture, UV radiation-induced damaged skin or photodamaged skin, hyperpigmented skin or melasmas, hypopigmented skin, dry skin, sagging skin, rough skin, and any combination thereof. Each possibility represents a separate embodiment. The compositions described herein may also be used for treating, preventing, minimizing, diminishing, or reversing the visible signs of scars such as, but not limited to, acne scars and chickenpox scars. Within the scope of the present invention is the treatment of aging skin, skin imperfections and scars. The term "treating" in the context of an epidermal condition related to aging includes at least one of the following: improving the firmness or elasticity of skin, smoothing of fine-lines or wrinkles, reducing skin pores, reducing hyperpigmentation or hypopigmentation, increasing skin thickness, radiance and/or softness, and reducing dry skin. Each possibility represents a separate embodiment. Treatment of the condition can be assessed as is known in the art and includes, a beneficial outcome or improvement that is manifested by enhancement in the appearance of the skin, for example by decreasing the appearance of wrinkles. This includes, for example, reducing oxidative damage in the skin.

As used herein the term "about" refers to ±10%.

The terms "comprise", "comprising", "include", "including", "having" and their conjugates mean "including, but not limited to".

As used herein, the singular forms "a", "an" and "the" include plural references unless the context clearly dictates otherwise. For example, the term "a peptide" or "a carrier" may include a plurality of peptides and carriers, including mixtures thereof.

Throughout this application, various embodiments of the invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

EXAMPLES

Reference is now made to the following examples, which together with the above descriptions, illustrate the invention in a non-limiting fashion.

Example 1

Different mole ratios of PFD5 sodium to HCl were generated by dissolving the peptide in an HCl solution using a magnetic stirrer. Following a few minutes of mixing, hydrogel formation was tested (Table 2). Compositions containing 1% (w/v) of PFD5 at a concentration of 6 mM (equivalent to 36 mM COO$^-$), resulted in stable hydrogels with the addition of 18 mM HCl. Hence, in order to obtain a clear and homogeneous hydrogel, the mole ratio of the peptide to acid was determined to be at least 1:3.

Compositions containing 2.5% (w/v) of PFD5 at a concentration of 15 mM (equivalent to 90 mM COO$^-$) resulted in stable hydrogels with the addition of 30 mM HCl. Hence, in order to obtain a clear and homogeneous hydrogel at this peptide concentration, the mole ratio of the peptide to acid was determined to be 1:2.

Compositions containing 4.8% (w/v) of PFD5 at a concentration of 28.8 mM (equivalent to 173 mM COO$^-$) resulted in stable hydrogels with the addition of 48 mM HCl. At this peptide concentration, the mole ratio of the peptide to acid was determined to be 1:1.67 to afford a stable clear hydrogel.

TABLE 2

| Formulation | Peptide % w/v | peptide mM | COO$^-$ mM | HCl mM | Molar Ratio peptide:acid | pH | Gel assessment HD | Gel assessment Clarity |
|---|---|---|---|---|---|---|---|---|
| #1 | 1 | 6 | 36 | 1 | 1:0.17 | 6.68 | N | Y |
| #2 | 1 | 6 | 36 | 4 | 1:0.67 | 6.08 | N | Y |
| #3 | 1 | 6 | 36 | 12 | 1:2 | 5.98 | N | Y |
| #4 | 1 | 6 | 36 | 18 | 1:3 | 5.95 | Y | Y |
| #5 | 1 | 6 | 36 | 24 | 1:4 | 5.44 | Y | O |
| #6 | 1 | 6 | 36 | 36 | 1:6 | 4.11 | N | O |
| #7 | 2.5 | 15 | 90 | 2.5 | 1:0.15 | 6.61 | N | Y |
| #8 | 2.5 | 15 | 90 | 10 | 1:0.67 | 6.39 | N | Y |
| #9 | 2.5 | 15 | 90 | 30 | 1:2 | 6.37 | Y | Y |
| #10 | 2.5 | 15 | 90 | 45 | 1:3 | 5.99 | Y | O |
| #11 | 2.5 | 15 | 90 | 60 | 1:4 | 5.46 | Y | O |
| #12 | 2.5 | 15 | 90 | 90 | 1:6 | 3.95 | Y | O |
| #12a | 3.75 | 22.5 | 135 | 45 | 1:2 | 6.33 | Y | Y |
| #12b | 4.8 | 29 | 174 | 48 | 1:1.6 | 6.7 | Y | Y |

HD: Hydrogel formation; Y = Yes; N = No; O = Opaque.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Example 2

Rheology data of a composition containing PFD5 (SEQ ID NO: 1) at 2.5% w/v in 45 mM HCl was compared to a commercial hyaluronic acid (HA), cross linked, dermal filler.

Figure 1B:
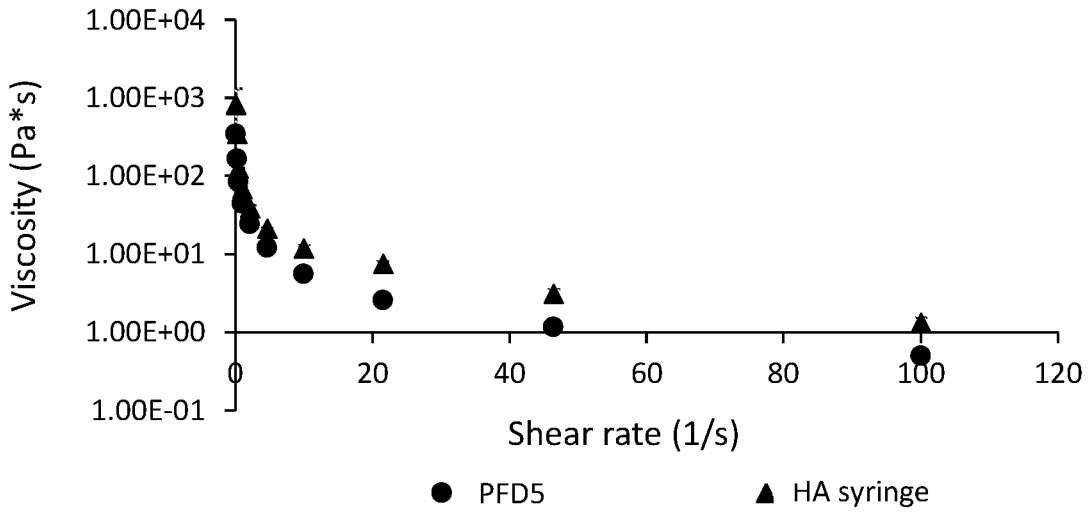

Viscoelastic properties of hydrogels were measured by dynamic frequency sweep tests on Rheometer AR 2000 TA instruments operating in cone plate mode with a cone angle of 4° and 20 mm diameter. The linear region was first determined by stress sweep measurements at a constant angular frequency of 6.3 rad/s. The elastic and loss moduli, G' and G" were extracted from frequency sweeps in the range 0.5-100 rad/s, performed at the linear stress region. The results are presented in FIGS. 1A-1B.

Figure 2A:
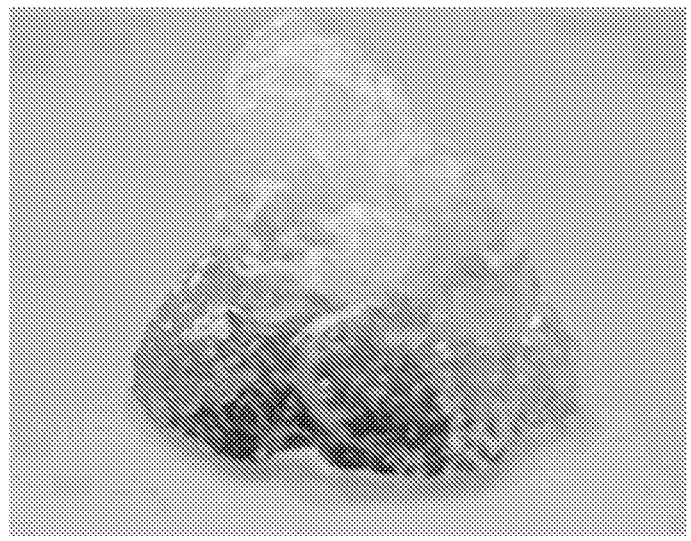
FIGS. 2A-2B. Images of commercial crosslinked hyaluronic acid (2A) and PFD5 2.5% w/v hydrogel (2B), each injected using a 27 gauge needle, showing a smoother texture of the PFD5 hydrogel.
Figure 2B:
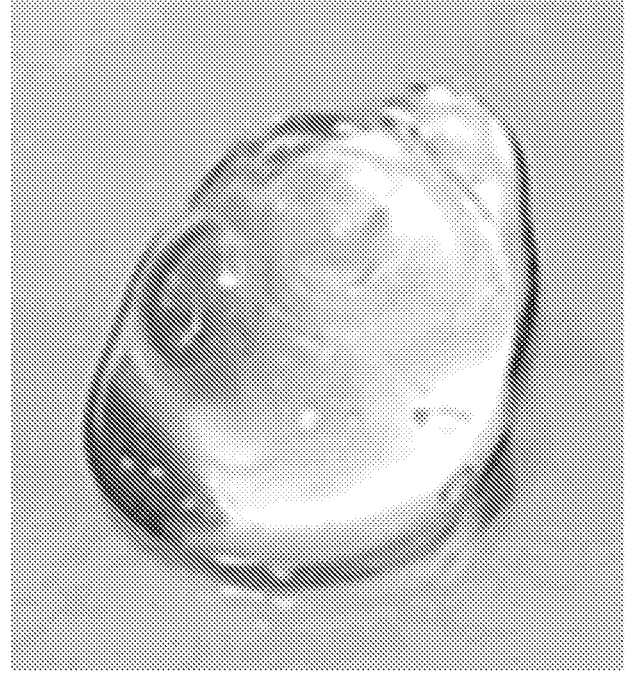
Figure 3A:
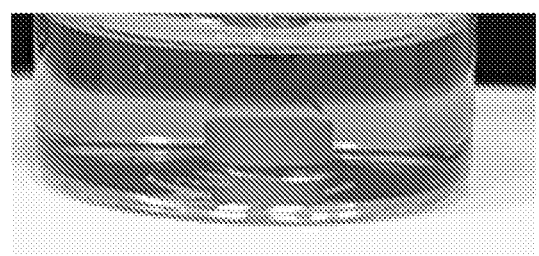
FIGS. 3A-3H. Images of commercial crosslinked hyaluronic acid and PFD5 2.5% w/v hydrogels, incubated in fetal calf serum for different periods of time showing almost no swelling and dissolution of the PFD5 hydrogel, and significant swelling with complete dissolution of the hyaluronic acid hydrogel. (3A) PFD5 hydrogel in fetal calf serum at T=0; (3B) crosslinked hyaluronic acid in fetal calf serum at T=0; (3C) PFD5 hydrogel at T=0; (3D) crosslinked hyaluronic acid at T=0; (3E) PFD5 hydrogel in fetal calf serum at T=17 hours; (3F) crosslinked hyaluronic acid in fetal calf serum at T=17 hours; (3G) PFD5 hydrogel taken out of fetal calf serum after 17 hours; (3H) PFD5 hydrogel taken out of fetal calf serum after 64 hours.
Figure 3B:
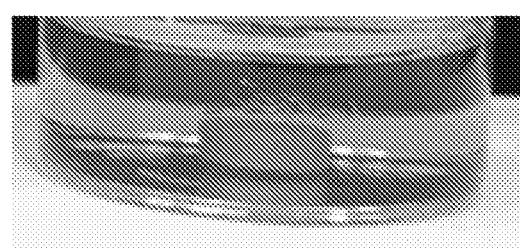
Figure 3C:
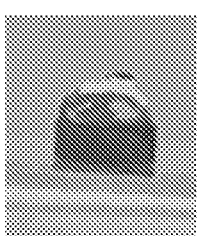
Figure 3D:
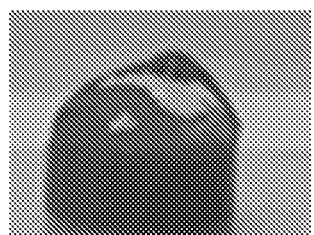
Figure 3E:
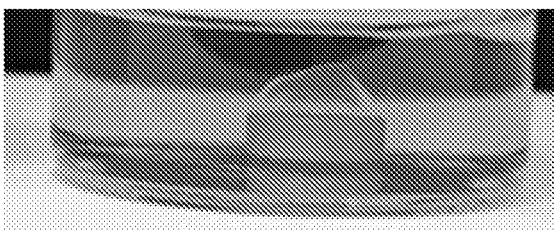
Figure 3F:
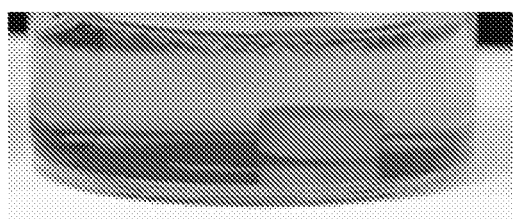
Figure 3G:
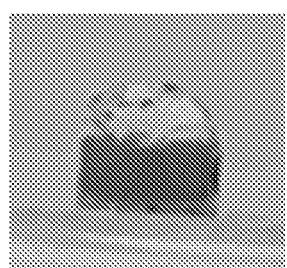
Figure 3H:
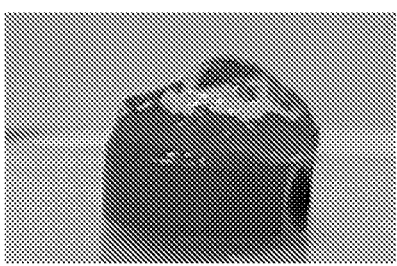

The two formulations were injected using a 27 gauge needle. FIG. 2A shows an image of a commercial cross-linked HA hydrogel and FIG. 2B shows an image of a PFD5 2.5% w/v hydrogel. The images show similarity in lifting potential of the hydrogels.

Images of commercial crosslinked-HA and PFD5 2.5% w/v hydrogel, incubated in fetal calf serum for different periods of time are shown in FIGS. 3A-3H. For ease of handling, hydrogels were placed on metal discs that could be taken out of the serum and imaged when placed on a glass slide. The images demonstrate cohesiveness and slow dissolution or degradation of PFD5 hydrogel noticeable to the naked eye at 17 h and 64 h. HA hydrogel seemed to have lost cohesivity at 17 h. Accordingly, no images were taken of the HA hydrogel after being taken out of the fetal calf serum at 17 h and 64 h. Net weight of gels on metal discs were measured over time. The results are presented in Table 3 below:

TABLE 3

| | Gels mass (mg) on discs | | | | |
| | T = 0 | T = 1 h | T = 4 h | T = 17 h | T = 64 h |
|---|---|---|---|---|---|
| PFD5 | 48.1 | 45.7 | 45 | 44.9 | 46 |
| Crosslinked HA | 49.3 | 0 | 0 | 0 | 0 |

Example 3

In order to test the potential irritation effects of the formulation according to certain embodiments of the present invention, an intracutaneous reactivity test was performed. Two extracts of a 3% w/v PFD5 hydrogel sample, one in a non-polar vehicle, cottonseed oil, and one in a polar vehicle, sodium chloride injection (0.9%), were prepared by immersing the sample in the relative solvents in order to reach a weight/volume ratio of 0.2 g/ml and incubating at $37\pm1°$ C. for $72\pm2$ h in dynamic conditions (orbital stirrer). 0.2 ml of the two extracts and 0.2 ml of the respective solvents were intracutaneously injected in five sites of 3 albino rabbits, and macroscopical skin reactions, as erythema, oedema and eschar were evaluated. No abnormalities immediately after intradermal injection of sodium chloride injection extract and sodium chloride injection (vehicle control) were observed. In all sites treated with sodium chloride injection extract and in all control sites treated with sodium chloride injection of all animals, no signs of erythema or oedema were detected 24, 48 and 72 hours after the treatment. The primary irritation index in sodium chloride injection (Treated-Control) was 0.00. No abnormalities immediately after intradermal injection of cottonseed oil extract and cottonseed oil (vehicle control) were observed. In all sites treated with cottonseed oil extract and in all control sites treated with cottonseed oil of all animals, a slight erythema and a slight oedema were detected 24, 48 and 72 hours after the treatment. The primary irritation index in cottonseed oil (Treated-Control) was 0.00.

Example 4

In order to test the local implantation effects of a 3% w/v PFD5 formulation according to certain embodiments of the present invention, an implantation test was performed.

10 albino rabbits were used for the test: each animal was implanted with the test sample at the right femur and with negative control (USP reference standard control plastic, HDPE) at the left femur, for a total of two sites/animal.

Figure 4:
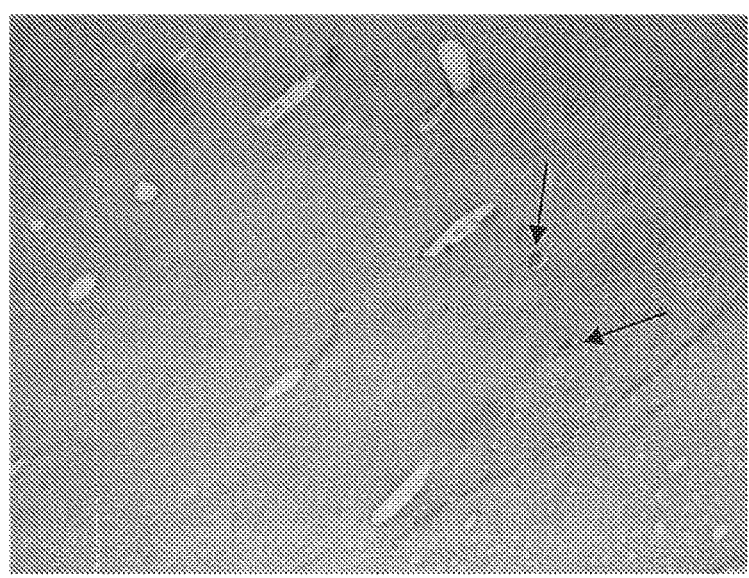
FIG. 4. A histological section (H&E staining) of a tissue implanted with a PFD5 containing formulation. The arrows indicate new blood vessels within the regenerated tissue.

One explant time was scheduled after 4 weeks. Animals were daily submitted to general objective exam with the purpose to detect possible local effects due to the sample. The behavior of animals was observed and all abnormalities were recorded. During the explant, all implanted sites with the test sample and with the negative control were harvested and observed macroscopically to determine any injuries. Implantation sites of each animal and local lymph nodes were preserved in formalin 10% buffer solution and used for histological evaluation. During the daily observations (general objective exam), all animals did not show any local effect. Nothing abnormal was detected macroscopically in both treated and control sites of all animals. Minimal local effects compared to the negative control, 4 weeks after implantation were determined. Such minimal local effects are mainly related to a minimal neovascularization at the treated sites which has been found also at the control sites. Furthermore, no inflammatory responses or necrosis have been observed at the sites of implantation. FIG. 4 shows tissue regeneration following implantation of test item demonstrated by H&E staining histological section. Complete resorption with neovascularization is noticed.

Example 5

In order to test the efficacy of the hydrogel according to certain embodiments of the present invention as a dermal filler, an in-vivo duration evaluation of the hydrogels by histology is performed. 100 µl bolus injections of hydrogels of the invention are implanted subcutaneously in the dorsal surface of Sprague Dawley rats. Commercial crosslinked HA gels are used as controls. The implants are removed at 1, 4, and 18 weeks and analyzed by histology with hematoxylin and eosin (H&E) staining. Sections are taken at the injection sites. Two sections are cut from each tissue sample and the H&E stained section is stitched using a stitching scope. The samples are then grouped and scored as follows; none (0%), low (25%), medium (50%), and high (100%) depending on the amount of material remaining.

Example 6

In order to test the efficacy of the hydrogel according to certain embodiments of the present invention as a dermal filler, an in-vivo duration evaluation of the hydrogels by Magnetic Resonance Imaging (MRI) is performed. MRI evaluates the volume and surface area change with time of hydrogels according to certain embodiments of the present invention and commercial crosslinked HA hydrogels over a period of 40 weeks, after intradermal injections in female Sprague-Dawley rats.

The gels are injected at a target volume of 150 µl per implant. Implants are located at two contralateral sites slightly caudal to shoulder, two contralateral sites slightly rostral from knee, and two contralateral sites midpoint between head and tail. MRI scans are performed on a 300 MHz Bruker Biospec MRI scanner. Images are collected on the day of implantation (week 0), and at 12, 24, 40 weeks after implantation. Absolute volume of gel at the implantation site is determined.

Example 7

Figure 5A:
FIGS. 5A-5B. (5A) Images of hydrogels composed of PFD5 at 1.5, 2, 2.5, 3, 3.5, and 5% w/v (two vials per each peptide concentration) in inverted vials placed in front of a paper printed with a line showing increased turbidity with increased PFD5 concentrations; (5B) Turbidity of the hydrogels measured by light absorption at 600 nm.
Figure 5B:
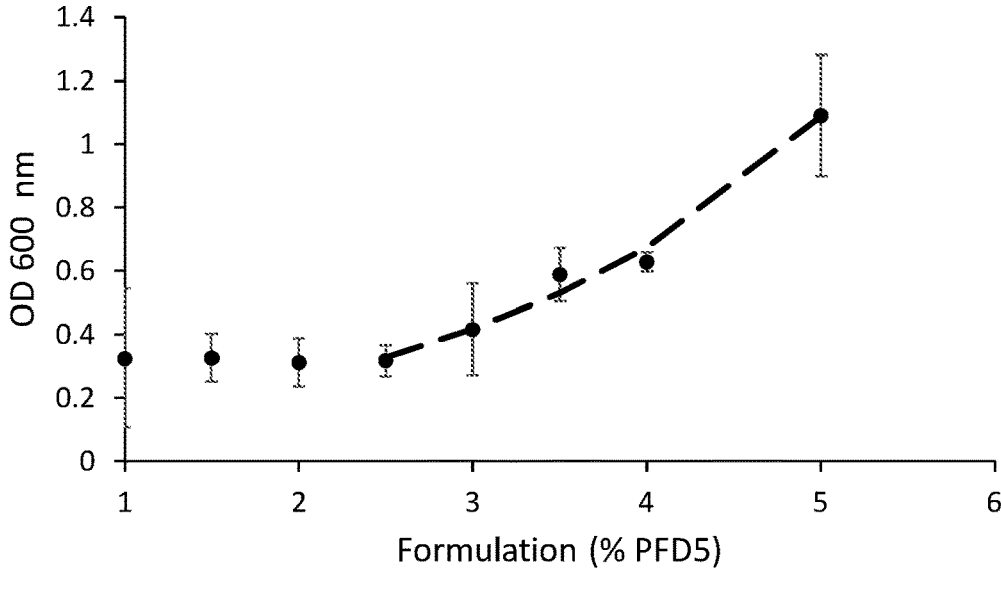

Hydrogels were prepared by mixing PFD5 solution with an HCl solution at different concentrations to obtain hydrogels with peptide concentrations of 1.5-5% w/v and a final pH of $5.9\pm0.05$. Hydrogel formation was first assessed by flipping over the vials in which hydrogels were prepared. FIG. 5A shows images of inverted vials containing the self-sustained hydrogels. These images demonstrate that the content of the vials resists flowing thereby indicating a solid-like behavior of the formed hydrogels. The clarity of the gels was demonstrated by placing the vials in front of a printed line and visualizing the quality of the line reflected through the hydrogels in the vials. The quality of the line, reflected through the vials, demonstrates the hydrogels' transparency/clarity. The more concentrated hydrogels appeared to be more opaque (FIG. 5A). Turbidity of the hydrogels was measured by a spectrophotometer at 600 nm (FIG. 5B) and shown to increase with increasing PFD5 concentrations.

Example 8

Figure 6A:
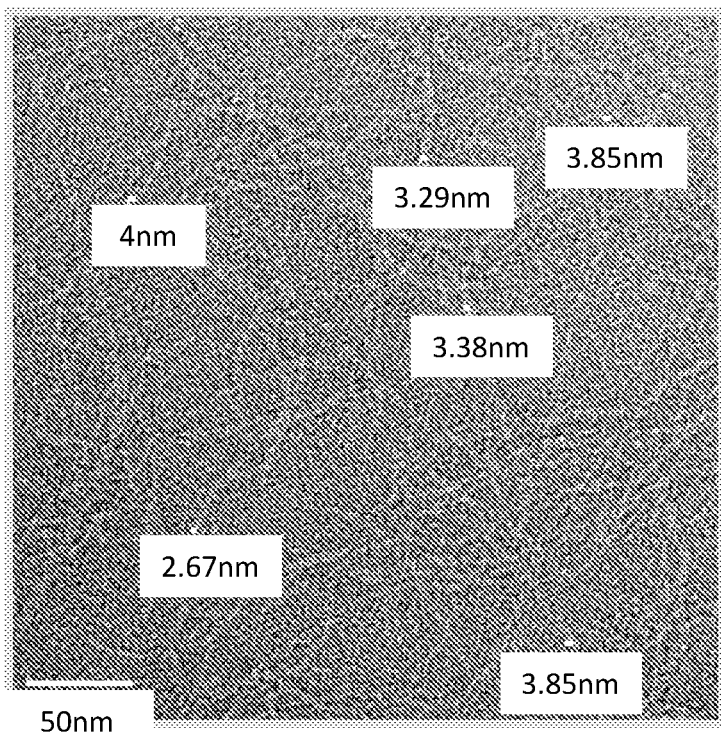
FIGS. 6A-6B. TEM micrographs of a PFD5 hydrogel according to certain embodiments of the present invention showing dimensions which correspond to PFD5 being in a β-sheet conformation and packed as a bilayer (6A) and a hyaluronic acid-based hydrogel showing aggregates (6B).
Figure 6B:
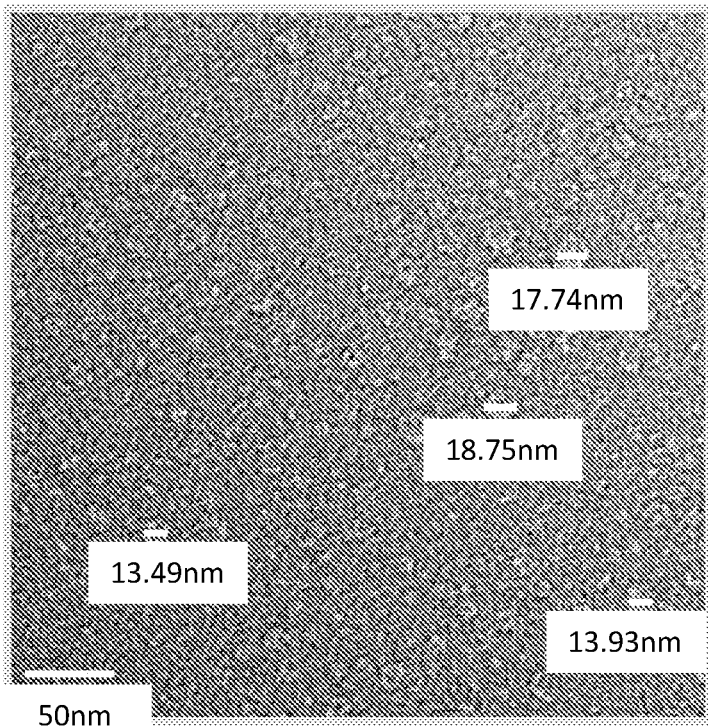

PFD5 3.5% w/v hydrogel and HA (Juvederm Ultra 3), each were dissolved in DIW (1:100 v/v). Ten microliters of each diluted sample was placed on a carbon coated copper grid, 300 mesh, and allowed to equilibrate at room temperature for 20 minutes. The grids were negatively stained with Uranyl-Less and imaged by Thermo Fisher Scientific (FEI) Talos F200C transmission electron microscope operating at 200 kV. The images were taken with Ceta 16M CMOS camera. PFD5 hydrogel was shown to exhibit fibrils having widths in accordance with the length of PFD5 in β-sheet conformation (0.345×13=4.5 nm) and exhibiting thicknesses of about 2 nm corresponding to a bilayer of peptides in a β-sheet conformation (FIG. 6A). The fibrils which appear entangled are contemplated to contribute to the elastic strength of the PFD5 hydrogels. In comparison, hyaluronic acid-based hydrogel (Juvederm Ultra 3) appeared to form a continuous dense layer over the grid with small (~15 nm) round shaped domains (FIG. 6B).

Example 9

Figure 7A:
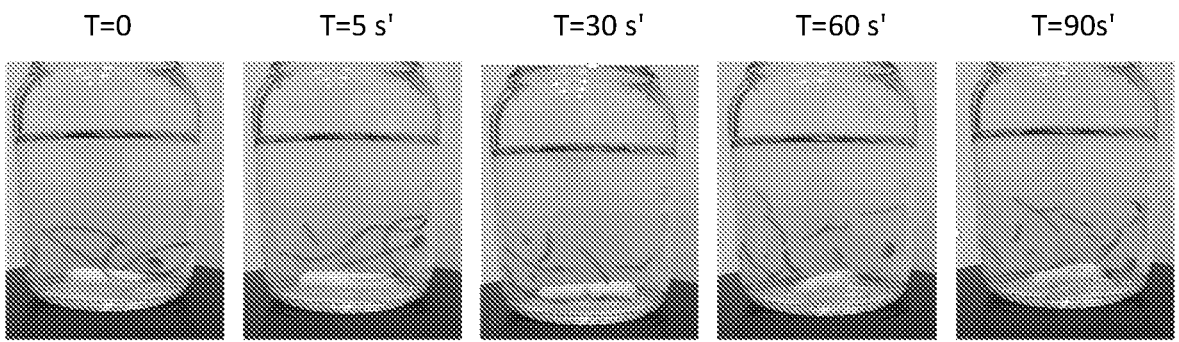
FIGS. 7A-7C. Images of vials containing hydrogels stained with methylene blue in cohesivity assessment at T=0, 5, 30, 60 and 90 seconds following injection into a buffer solution, showing stronger cohesivity of the PFD5 hydrogel. (7A) a PFD5 hydrogel according to certain embodiments of the present invention; (7B) Hyaluronic acid-based hydrogel (Teosyal Ultimate); (7C) Hyaluronic acid-based hydrogel (Juvederm ultra 3).
Figure 7B:
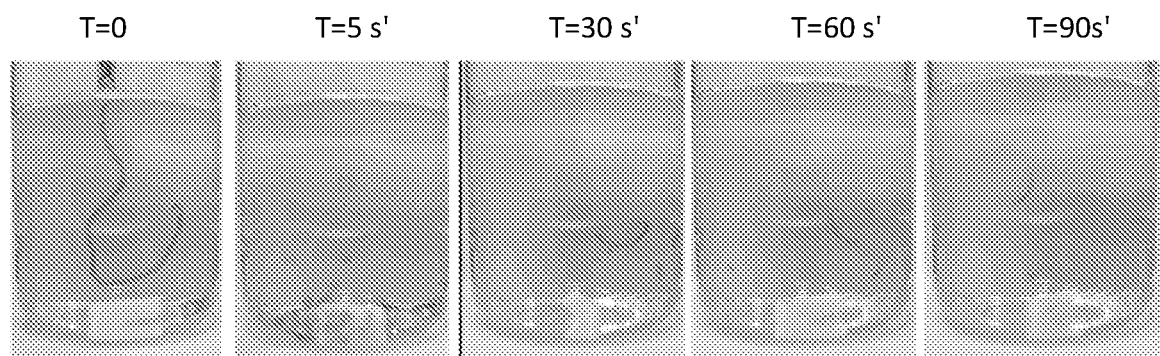
Figure 7C:
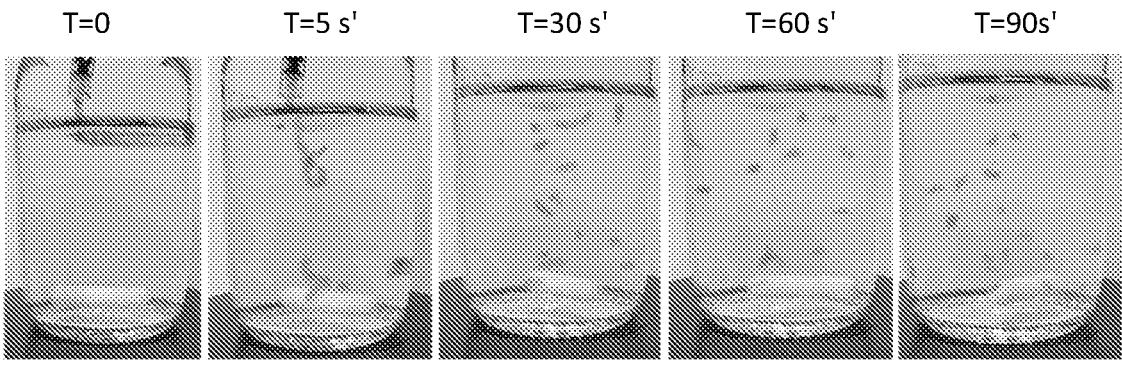

PFD5 hydrogels, 3.5% w/v, were mixed with methylene blue (1:25 v/v). The stained hydrogels (0.8 ml) were injected into a stirred beaker containing HEPES (20 mM) supplemented with 2.5 mM $CaCl_2$). Images were acquired at 0, 5, 30, 60 and 90 seconds (FIG. 7A). The cohesiveness of the PFD5 hydrogel was evaluated as 4.5 based on Gavard-Sundaram cohesivity 1-5 scale (Sundaram et al. Plastic and Reconstructive Surgery, 2015, 136(4): 678-686). In comparison, hyaluronic acid-based hydrogels (HA1, Teosyal Ultimate, FIG. 7B; and HA2, Juvederm ultra 3, FIG. 7C), that underwent a similar procedure were evaluated to have cohesiveness of 2 and 3 on the Gavard-Sundaram cohesivity scale.

Example 10

Figure 8A:
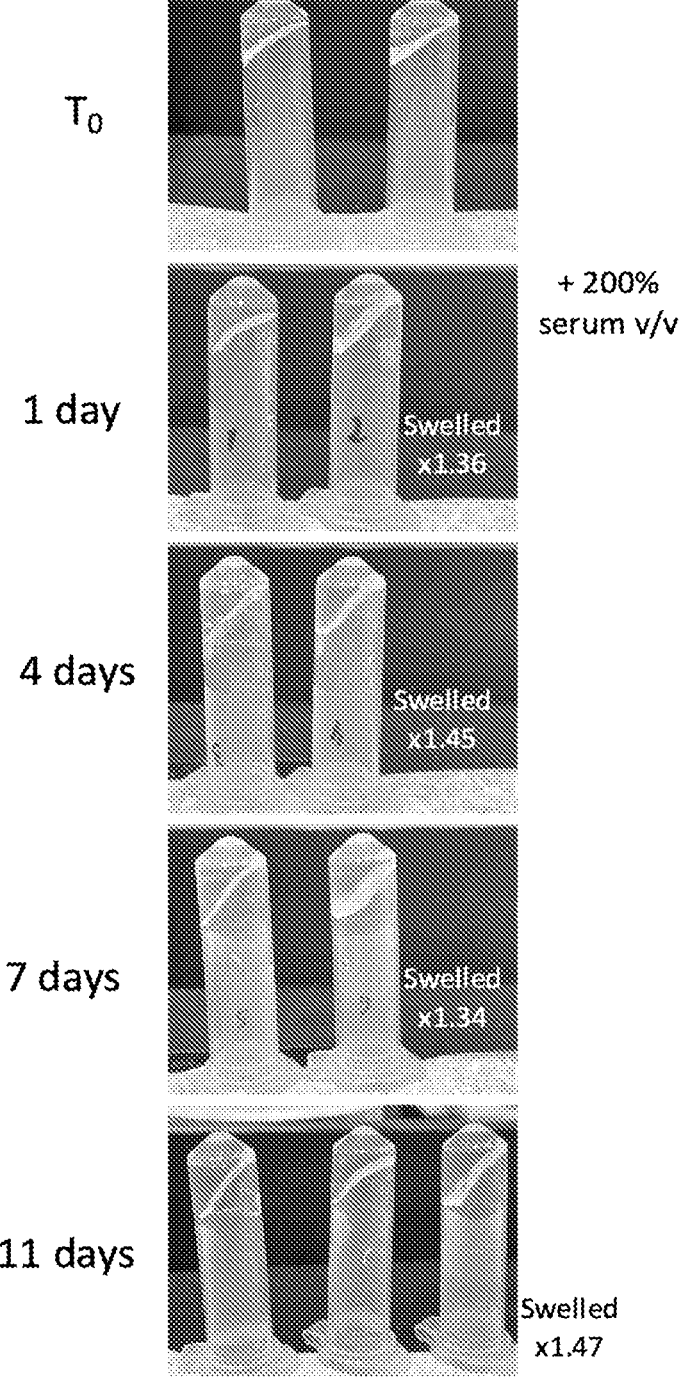
FIGS. 8A-8C. Images of inverted tubes containing hydrogels in swelling assessment using Fetal Bovine Serum (FBS) showing reduced swelling of the PFD5 hydrogel as compared to hyaluronic acid-based hydrogels. (8A) a PFD5 hydrogel according to certain embodiments of the present invention at T=0 and 1, 4, 7, and 11 days following incubation in 200% (v/v) serum with indicated swelling; Hyaluronic acid-based hydrogels of HA1 (8B) and HA2 (8C) at T=0 and 1 day following incubation and full swelling in 200%, 300%, and 400% (v/v) scrum.
Figure 8B:
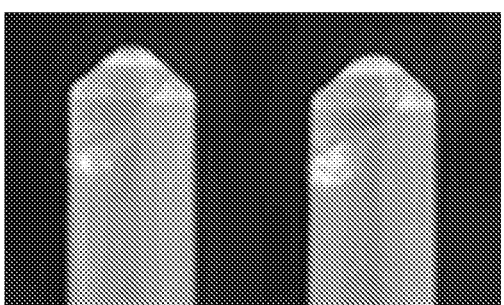
Figure 8B:
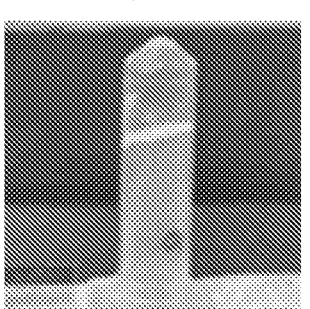
Figure 8B:
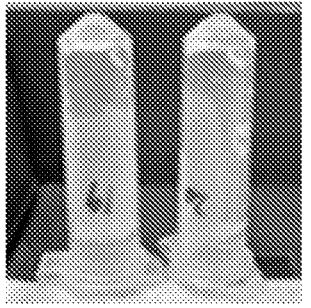
Figure 8B:
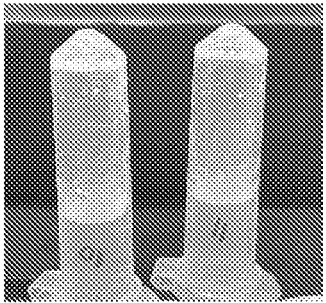
Figure 8C:
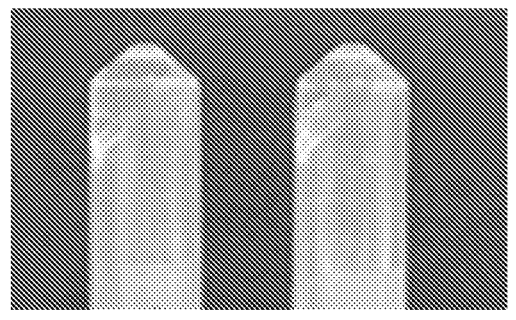
Figure 8C:
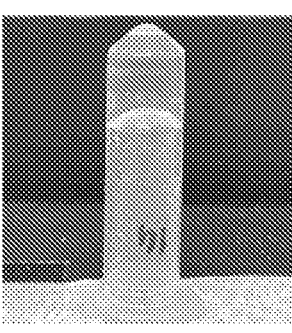
Figure 8C:
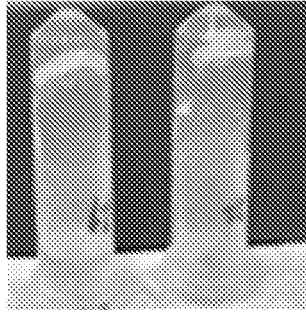
Figure 8C:
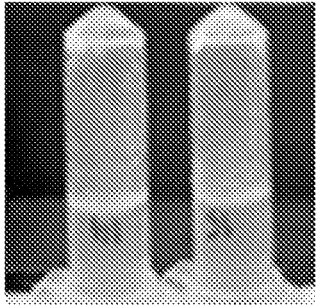

Fetal Bovine Serum (FBS) was added to tubes containing PFD5 2.5% w/v hydrogels at 1:2 v/v ratio. Tubes were incubated at 37° ° C. for different periods of time, i.e. 1, 4, 7 and 11 days. At each time-point, serum was removed and hydrogel mass remaining in the tube was measured. The swelling value was calculated based on the ratio (final hydrogel weight)/(initial hydrogel weight). PFD5 hydrogels incubated with 1:2 v/v FBS exhibited a constant ratio of swelling, ×1.3-1.5 w/w, independent of the incubation time. FIG. 8A shows inverted tubes demonstrating no flow of the serum incubated hydrogels. The same procedure was applied to PFD5 1.5-5% w/v hydrogels which showed similar swelling ratios of 1:1.2 up to 1:1.5 v/v (namely, ×1.2-1.5). In comparison, hyaluronic acid-based hydrogels HA1 (Teosyal Ultimate) and HA2 (Juvederm ultra 3) which were supplemented with 1:2, 1:3 and 1:4 (HA:FBS) v/v and incubated for one day at 37° ° C., swelled to 2-4 times their initial volume, respectively (FIGS. 8B-8C).

Example 11

Resistance of the hydrogels containing PFD5 (3.5% w/v) and HCl according to certain embodiments of the present invention to oxidation was assessed based on procedures detailed in https://doi.org/10.2147/CCID.S220227, and https://doi.org/10.1371/journal.pone.0218287 and compared to hyaluronic acid-based hydrogels containing 2.2% and 2.4% w/v of hyaluronic acid, designated HA1 and HA2, respectively. In particular, an oxidizing solution of 1,248 mM $H_2O_2$ (30%, Carlo Erra, catalog #412072) and 12.48 mM $CuSO_4$ in DIW, 0.17 ml, was added to syringes containing 0.4 ml of hydrogels (final volume ratio of solution to gel was 1:3.33 v/v). The mixtures were stirred with a spatula for 1 minute and incubated for 30 minutes at room temperature.

Each of the syringes (1 ml, BD, ref 309648) was connected to either a 27 or a 30 G needle and subjected to extrusion force measurements (Force Gauge, FG-5000A, Lutron). Piston velocity was manually controlled to move at 0.8 mm/sec velocity. Average extrusion force was calculated from recorded values. Independent measurements (n=2) were performed for PFD5 hydrogels. Single measurements (n=1) were performed for hyaluronic acid-based hydrogels.

Figure 9A:
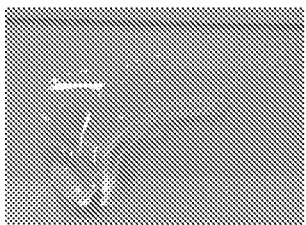
FIGS. 9A-9D. Images of oxidized hydrogels that were placed on glass slides, showing resistance to oxidation of the PFD5 hydrogel as opposed to loss of hydrogel rigidity of hyaluronic acid-based hydrogels under similar oxidative conditions. (9A-9B) HA1 and HA2; (9C) PFD5 hydrogel; (9D) PFD5 hydrogel on an inverted glass slide.
Figure 9B:
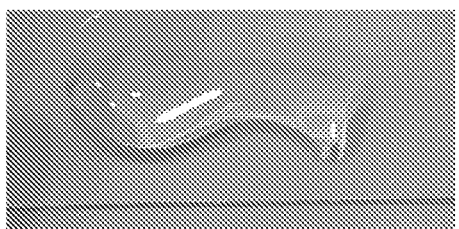
Figure 9C:
Figure 9D:
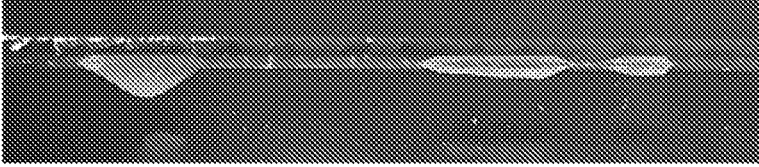

FIGS. 9A-9D show images of hydrogels that were exposed to oxidizing solutions. While the hyaluronic acid-based gels underwent oxidation and no longer resisted flow under gravitation force (9A-9B), the hydrogel containing PFD5 maintained the drop shape (FIG. 9C) even when the glass was flipped upside down (FIG. 9D).

Figure 10:
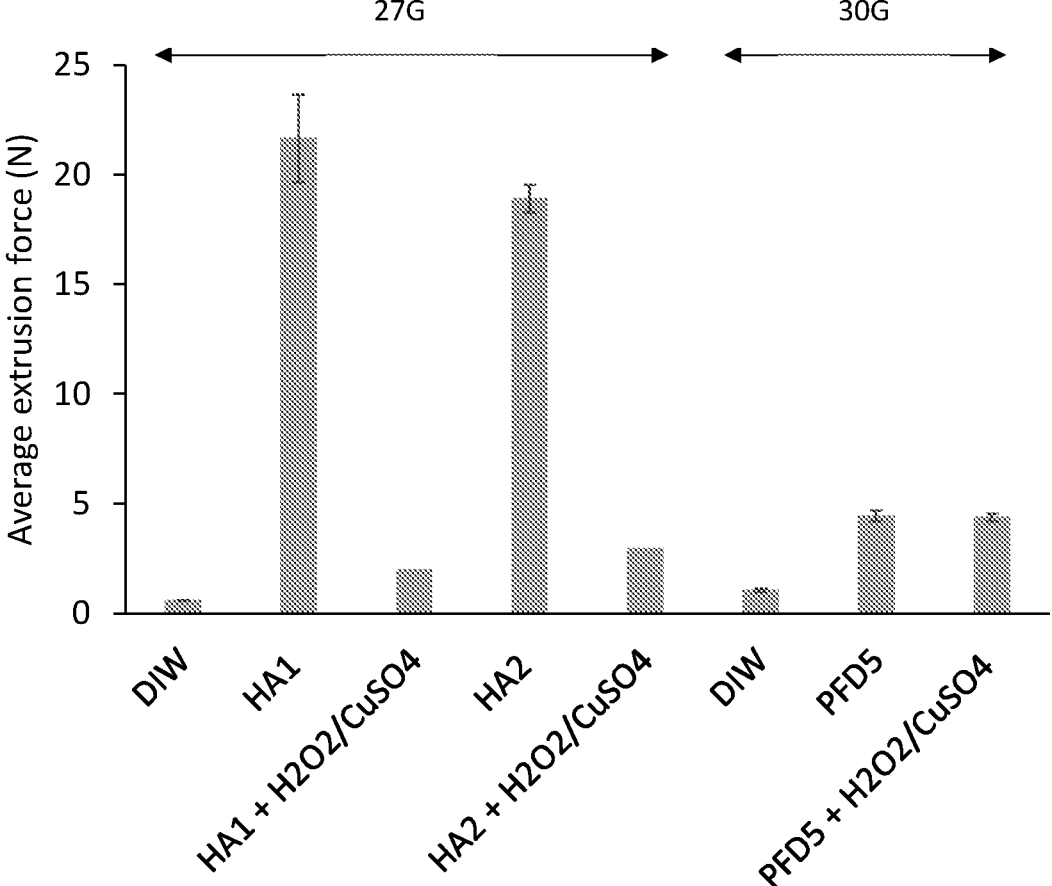
FIG. 10. Average of extrusion force measured through a 27G needle of: deionized water (DIW), HA1, oxidized HA1, HA2, and oxidized HA2; and through a 30G needle of: DIW, PFD5 and oxidized PFD5, showing that while the PFD5 hydrogel maintained its mechanical properties after exposure to oxidative conditions, the hyaluronic acid-based hydrogels lost their rigidity.

FIG. 10 shows that following the mixing of the hydrogels with the oxidating solution, the hydrogels according to certain embodiments of the present invention maintained their rigidity as indicated by the extrusion force measurement, whereas hyaluronic acid-based gels lost their rigidity and showed less than 20% of the extrusion force initial values prior to their oxidation.

Example 12

PFD5 3% w/v hydrogels were sterilized by autoclave, at 121° C. for 15 minutes. Viscoelastic properties of the hydrogels, before and after sterilization, were measured by dynamic frequency sweep test using AR 2000 T A Instruments, controlled stress rheometer, operating in cone and plate mode (cone angle 4° and 20 mm diameter).

Figure 11A:
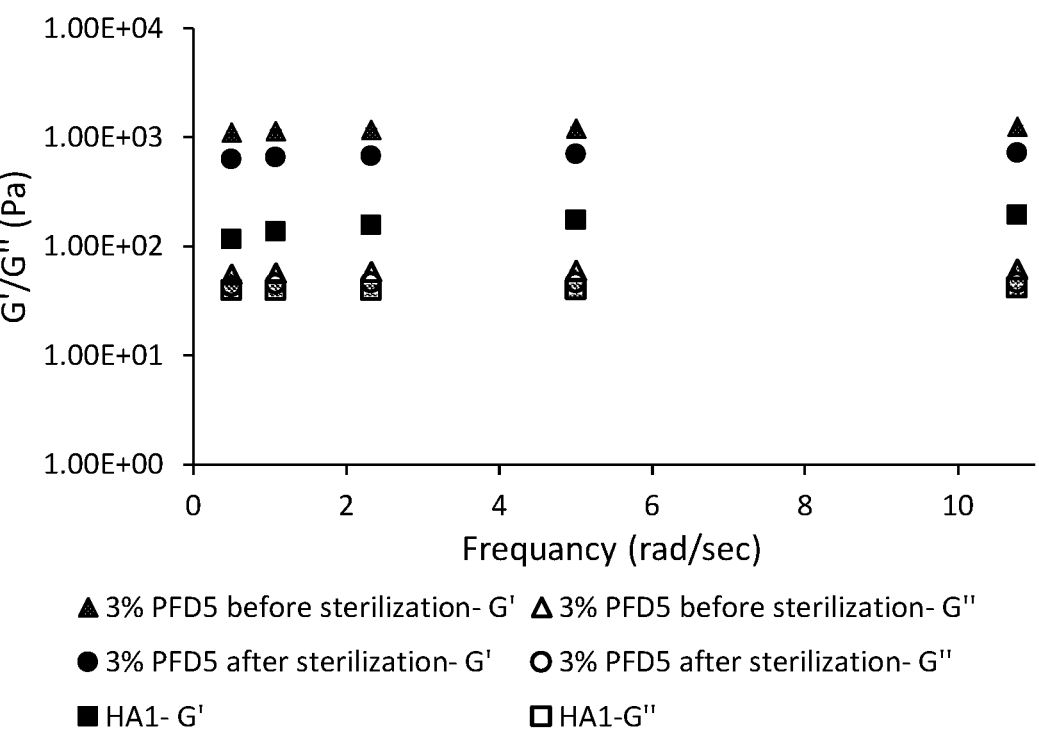
FIGS. 11A-11B. Rheological properties of PFD5 hydrogels according to certain embodiments of the present invention before and after sterilization as compared to a hyaluronic acid-based hydrogel (HA1), showing that sterilization has minimal effect on G' of the PFD5 hydrogel. (11A) G' and G"; (11B) Viscosity.
Figure 11B:
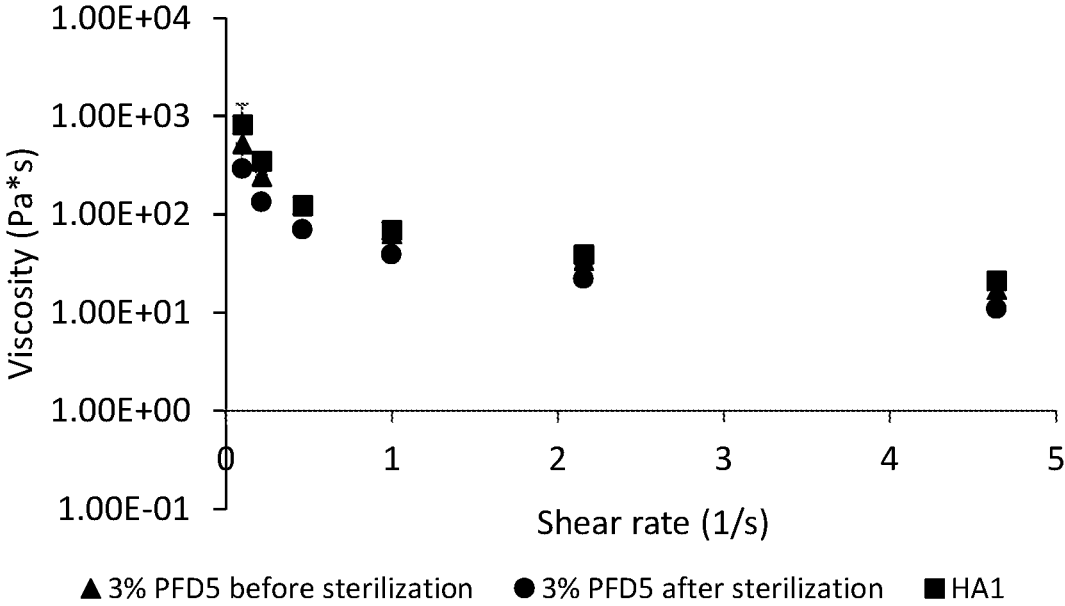

A small decrease in PFD5 hydrogel's rheological properties (G', G", viscosity) was observed after sterilization, suggesting that autoclave sterilization has minimal effect on hydrogel's rheological properties (FIGS. 11A-11B). PFD5-based hydrogel before and after sterilization showed higher G' and G" values as compared to hyaluronic acid-based hydrogel (HA1).

Example 13

Hydrogels were prepared by mixing PFD5 solution with HCl solution at different concentrations to obtain hydrogels with peptide concentrations of 1-5% w/v. Viscoelastic properties of the hydrogels were measured by dynamic frequency sweep test using AR 2000 controlled stress rheometer, operating in cone and plate mode (cone angle 4° and 20 mm

Figure 12A:
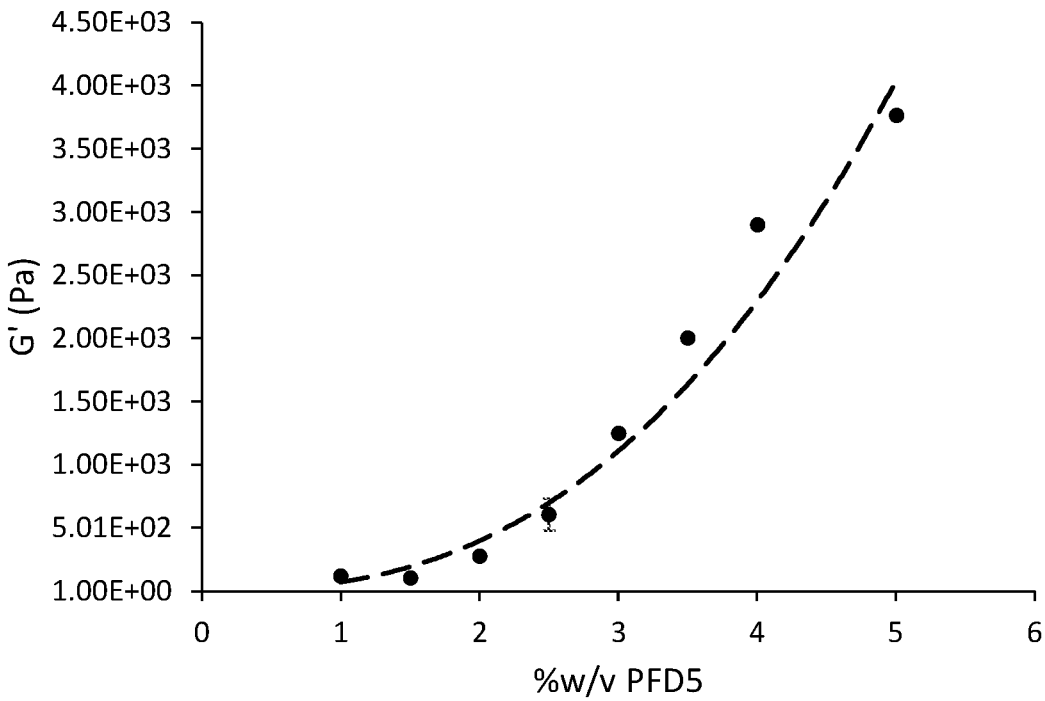
FIGS. 12A-12C. Viscoelastic properties of PFD5 hydrogels according to certain embodiments of the present invention, showing increased values of rheological moduli and viscosity with increased PFD5 concentrations. (12A) G' at 1 Hz; (12B) G" at 1 Hz; (12C) Viscosity at 1 Hz.
Figure 12B:
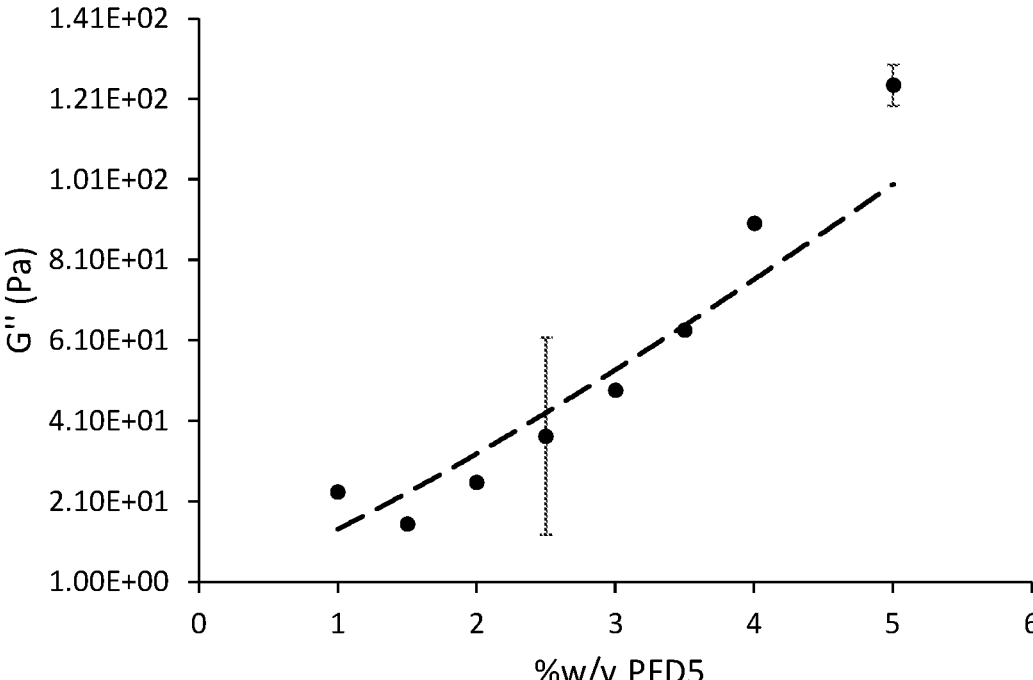
Figure 12C:
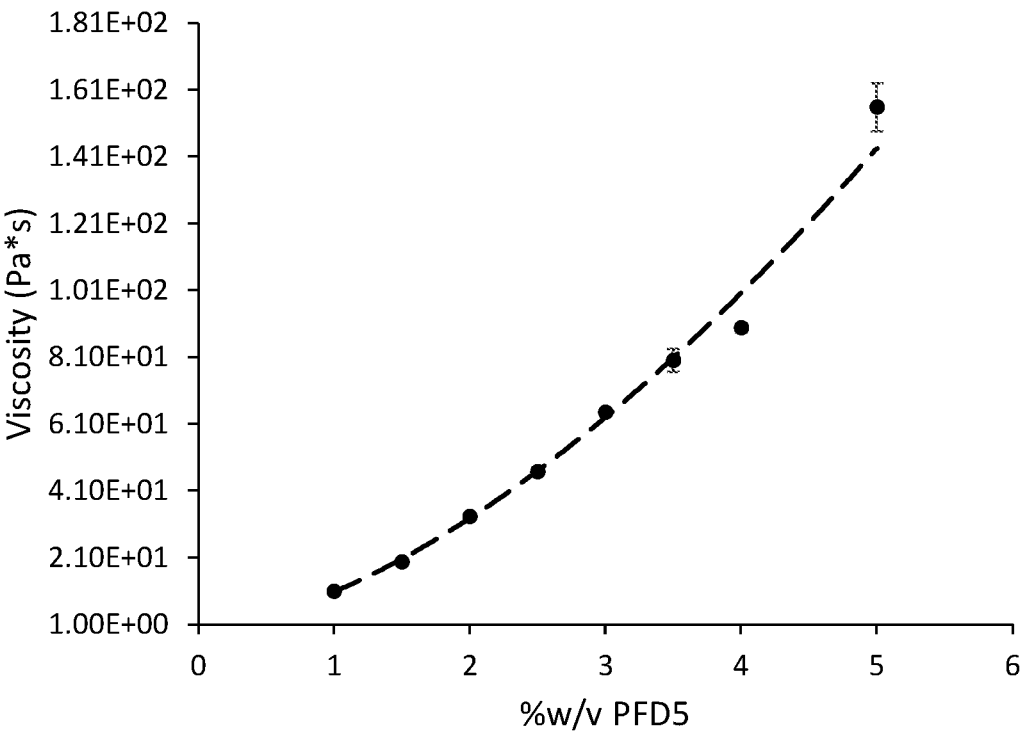

| diameter). Increased PFD5 concentrations resulted in higher G', G" and viscosity values (FIGS. 12A-12C, respectively).

Example 14

Figure 13A:
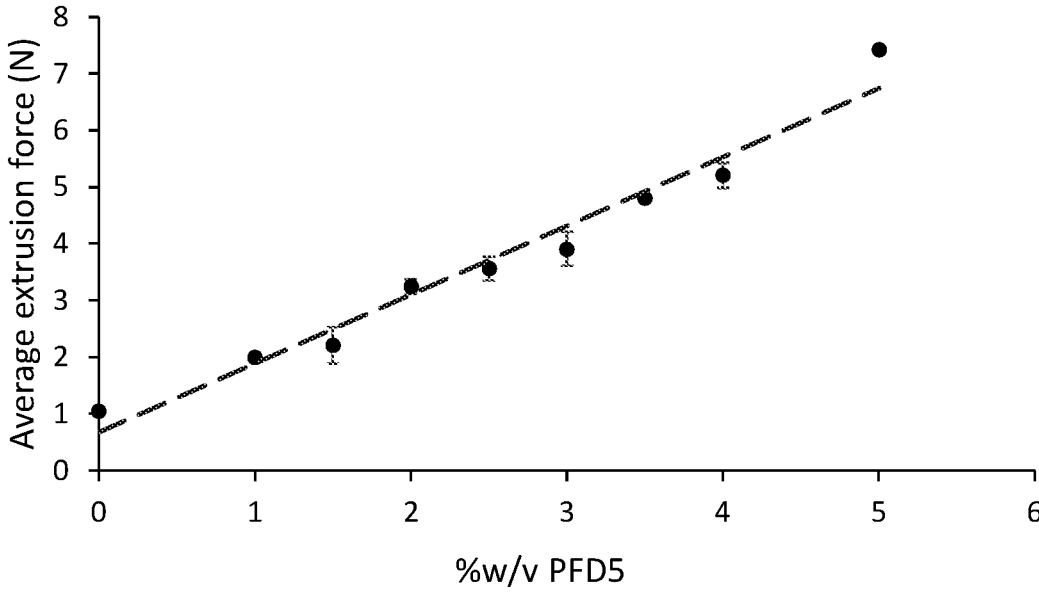
FIGS. 13A-13B. Average extrusion forces of PFD5 hydrogels according to certain embodiments of the present invention injected through a syringe with a 30 G needle, showing increased extrusion forces with increased PFD5 concentrations (13A) and full extrusion force profiles for PFD5 hydrogels as compared to a hyaluronic acid-based hydrogel (HA1) measured through a syringe with a 30 G needle, showing uniformity of PFD5 hydrogel injection and non-uniformity of HA1 hydrogel injection (13B).
Figure 13B:
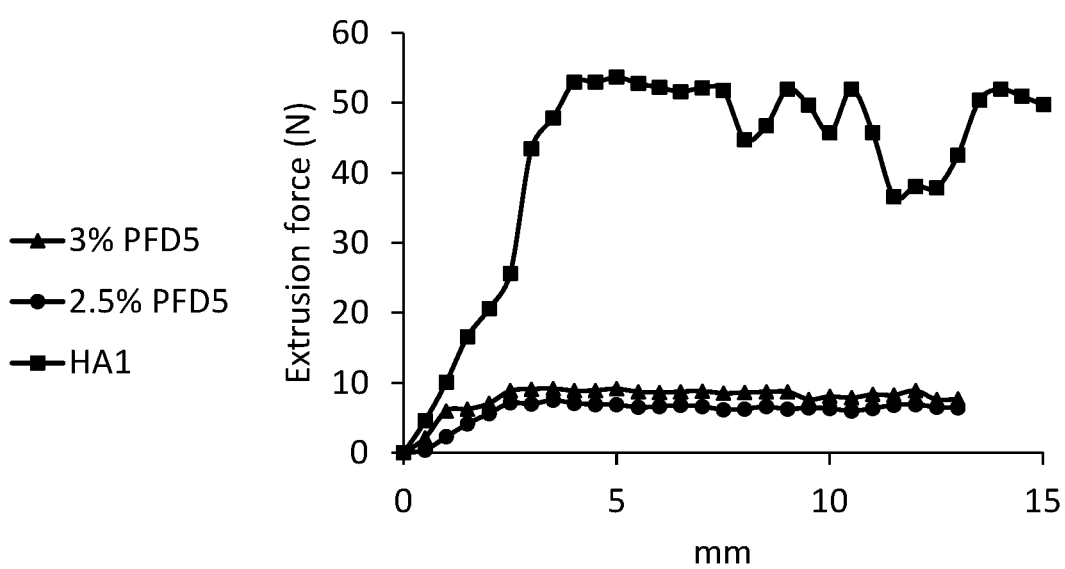

Hydrogels were prepared by mixing PFD5 solution with HCl solution at different concentrations to obtain hydrogels with peptide concentrations of 1-5% w/v. Extrusion force of water, i.e. 0% w/v PFD5, and of the hydrogels were measured using a force gauge (FG-5000A, Lutron) by lowering the piston and injecting 0.5 ml gel through a 30 G needle at a constant rate (1 ml/min). Higher extrusion forces were measured for more concentrated PFD5 hydrogels (FIG. 13A). Extrusion forces were found to linearly correlate with PFD5% w/v concentrations. Extrusion force was measured in a different syringe connected to a 27 G needle for comparing a hyaluronic acid-based hydrogel (HA1) with PFD5 (2.5 and 3% w/v) (FIG. 13B). HA1 exhibited a significantly higher average extrusion force 21.6 N, compared to ~8-9 N of the PFD5. Furthermore, while the extrusion force of HA1 exhibited a non-uniform pattern during injection (FIG. 13B), PFD5 hydrogel was injected more uniformly through the needle.

Example 15

Figure 14:
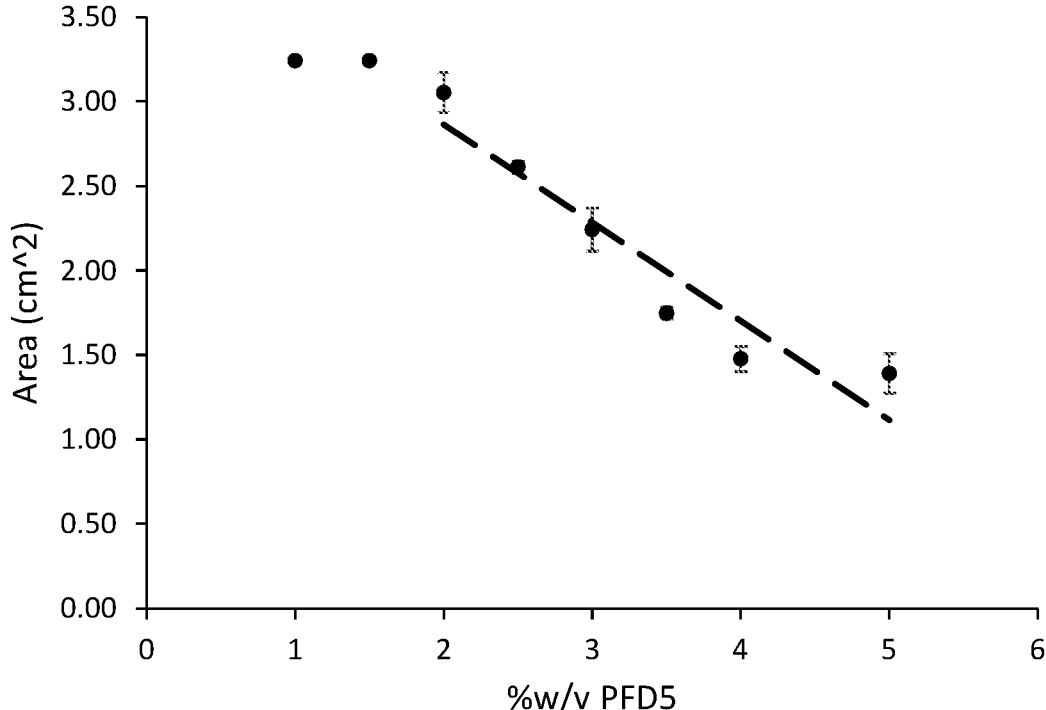
FIG. 14. Compaction measurement of a PFD5 hydrogel according to certain embodiments of the present invention showing smaller area occupied by the compacted PFD5 hydrogels as a function of concentration.

50 mg hydrogel were weighed on a small glass. Another glass was placed on top of the hydrogel on which a fixed weight (15 g') was placed over the top glass for 30 seconds. The compaction of the hydrogel due to the weight applied was recorded and the areas before and after compaction were measured by ImageJ software. FIG. 14 shows that for higher PFD5% w/v concentrations, the hydrogels are less spreadable, i.e. more cohesive.

Example 16

Figure 15A:
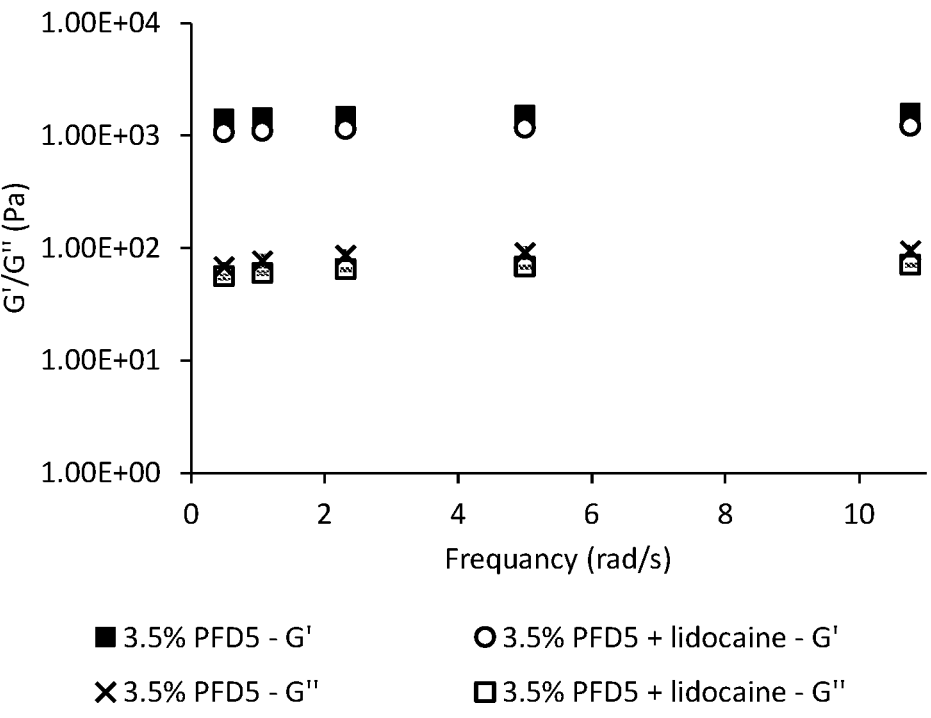
FIGS. 15A-15C. Rheological properties and extrusion forces of PFD5 hydrogels according to certain embodiments of the present invention with and without lidocaine, showing no influence of lidocaine on the rheological properties of PFD5. (15A) G' and G"; (15B) Viscosity; (15C) Extrusion force through a 30 G needle.
Figure 15B:
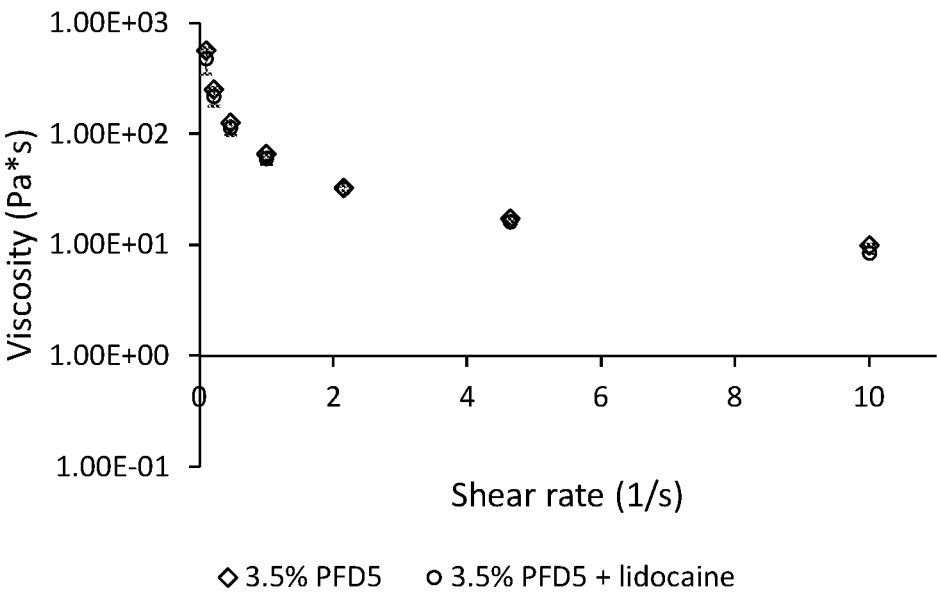
Figure 15C:
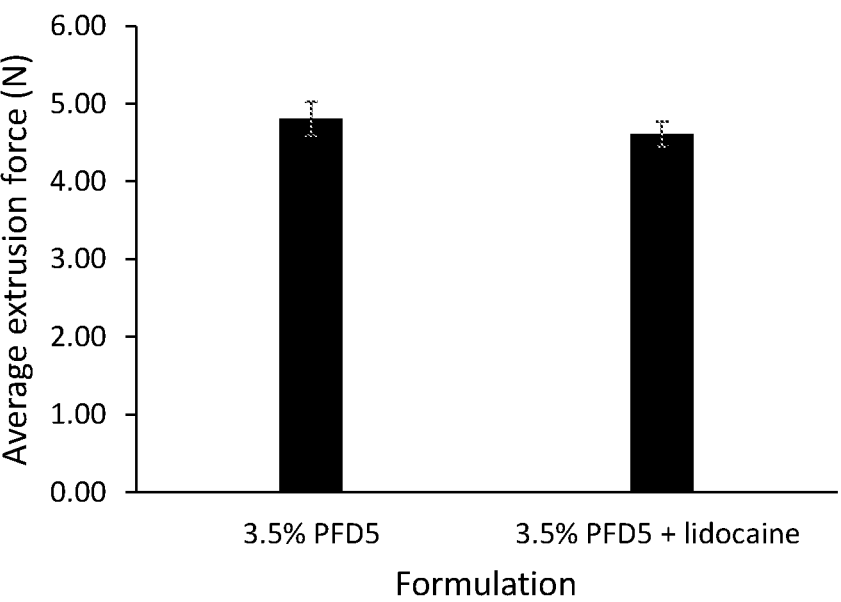

Lidocaine was dissolved in HCl 76 mM solution. The solution was mixed with PFD5 solution (1:1 v/v) to form PFD5 3.5% hydrogel with 0.3% lidocaine. PFD5 3.5% hydrogel with lidocaine showed similar rheological properties and extrusion forces, compared to PFD5 3.5% hydrogel with no lidocaine (FIGS. 15A-15C).

Example 17

Figure 16A:
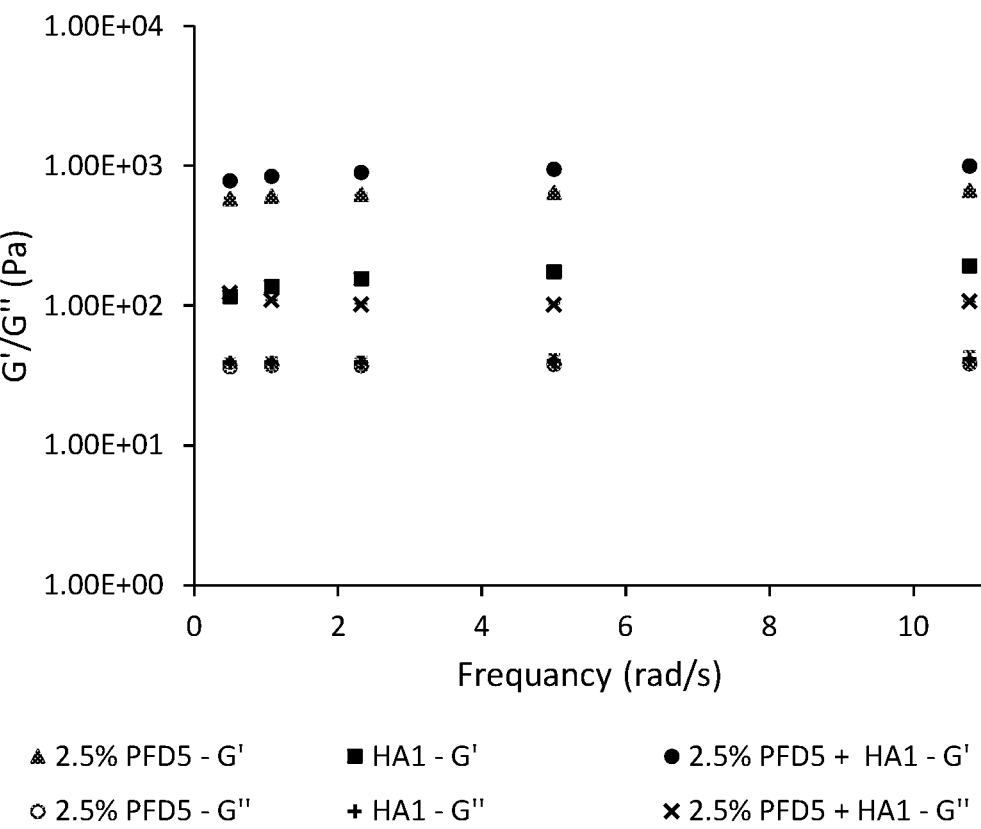
FIGS. 16A-16C. Rheological properties and extrusion forces of hydrogels containing a combination of PFD5 and hyaluronic acid showing that the combination provides higher rheological moduli and viscosity, and yet, lower extrusion force, as compared to hyaluronic acid hydrogel alone. (16A) G' and G"; (16B) Viscosity; (16C) Extrusion force through a syringe with a 27 G needle.
Figure 16B:
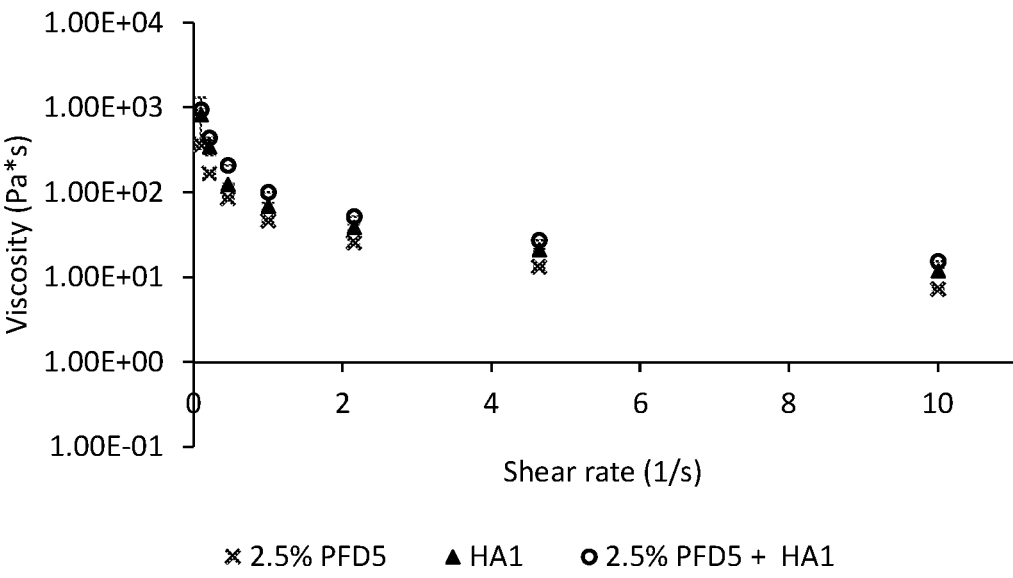
Figure 16C:
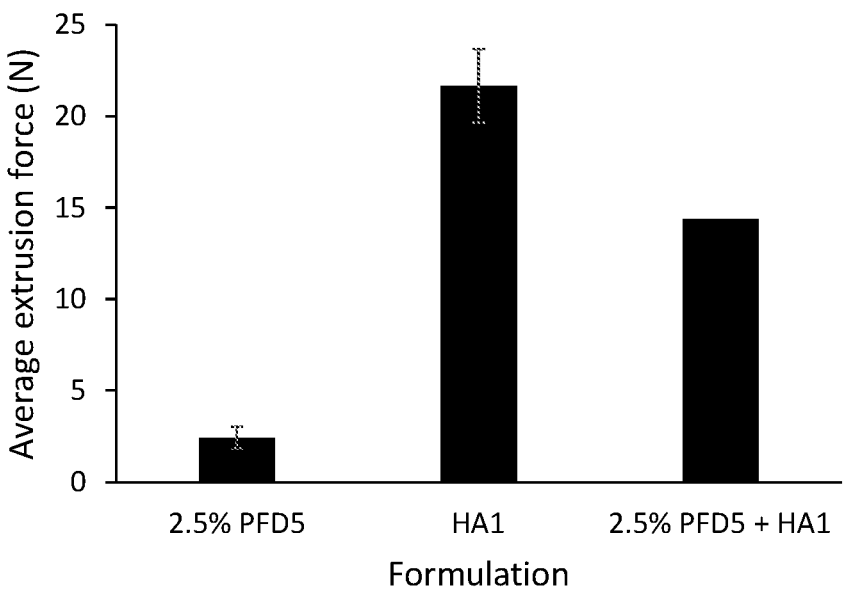

PFD5 5% hydrogel was mixed with HA1 (1:1 v/v) using two syringes to form a hydrogel composed of 2.5% PFD5 and HA1, each. The combined hydrogel demonstrated G' and viscosity values higher than that of each of the components alone (FIGS. 16A-16B) and an extrusion force lower than the extrusion force of HA1 alone (FIG. 16C).

Example 18

Figure 17:
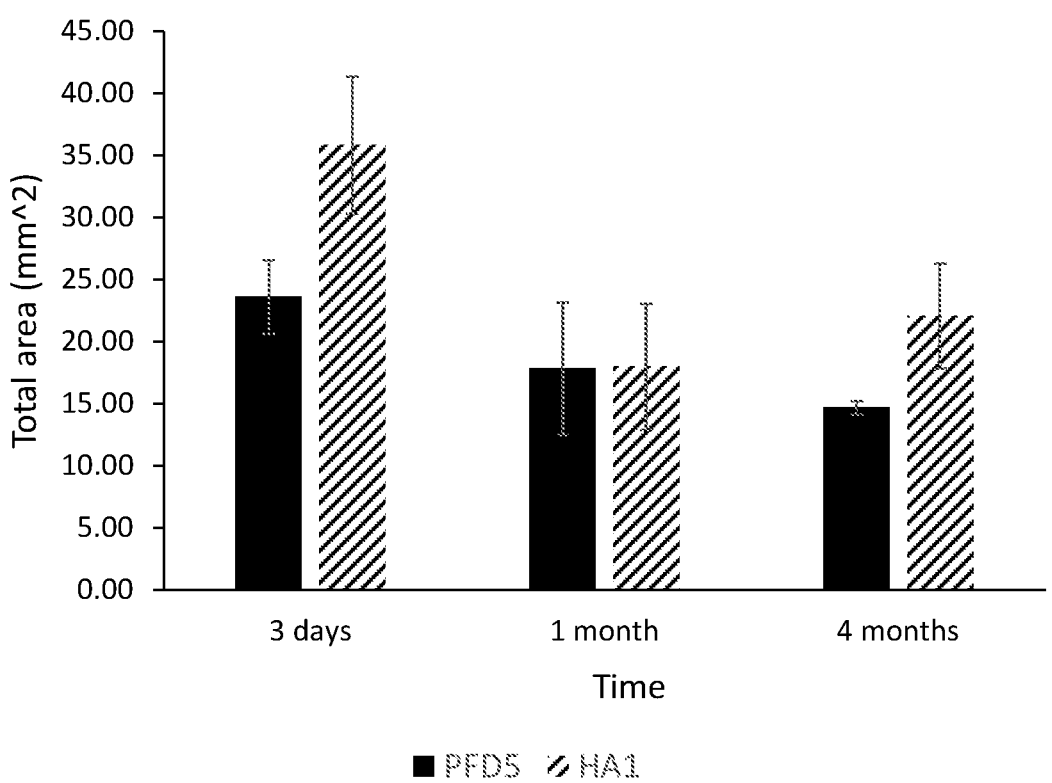
FIG. 17. Total area of an implant of PFD5 hydrogel according to certain embodiments of the present invention as compared to a hyaluronic acid-based hydrogel in a subcutaneous rat model.

The effect of PFD5 3.5% w/v hydrogel on tissue augmentation was tested in a subcutaneous rat model and compared to the effect obtained in rats treated with a commercially available hyaluronic acid dermal filler. Individual rats were treated with 0.2 ml of PFD5 hydrogel or HA injection administered subcutaneously above the parietal bone. Animals were held for three days, one month and four months after which implants were excised and underwent histological examination and analysis for the area occupied by the implant. Based on analysis of histological sections, PFD5 hydrogel showed an average area which is comparable to that occupied by the HA hydrogel (FIG. 17). Due to the lower swellability of the PFD5 hydrogel as compared to the HA hydrogel, the area remained more invariable.

Figure 18:
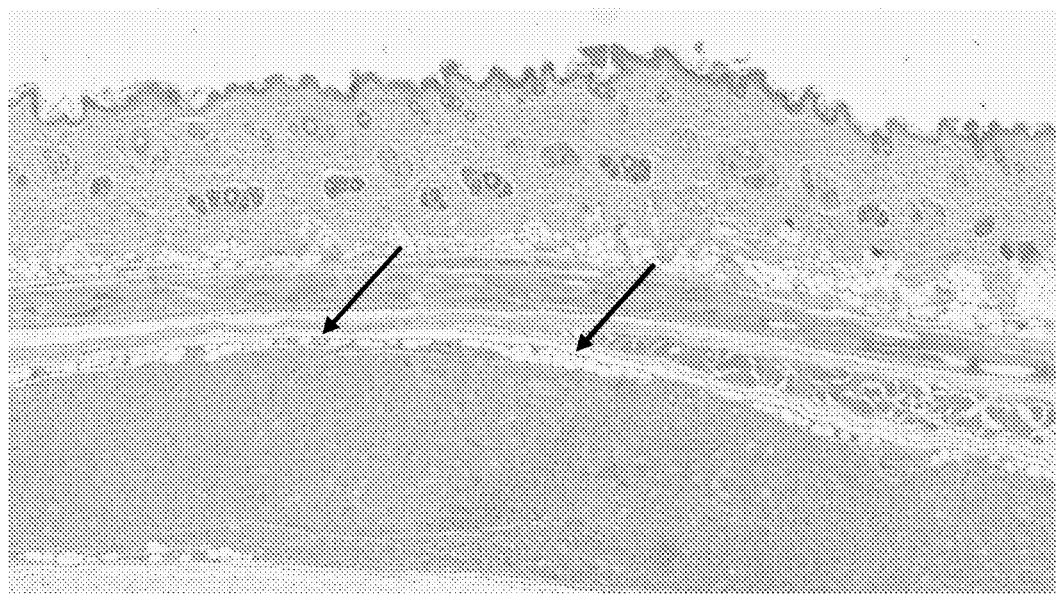
FIG. 18. A histological section of an implant obtained following subcutaneous injection of a PFD5 hydrogel according to certain embodiments of the present invention. The arrows indicate adipocytes in proximity to the implant.

The PFD5 hydrogel demonstrated full resorption by macrophages and continuous biodegradation, deprived of multinucleated giant cells or other adverse effects to nearby tissue. Furthermore, based on histology analysis, the implant supported adipocytes viability at its proximity (FIG. 18).

Example 19

PFD5 hydrogels are blended with human lipoaspirate in volume ratios of 5:95, 10:90, 25:75, 50:50, or 75:25 thereby forming lipo+gel grafts. Uniformity and stability of the grafts during incubation in a standard cell-culture incubator are assessed. Adipocytes' viability is also evaluated. The grafts are then tested in-vivo using a subcutaneous implant model in athymic rats. As control, human lipoaspirate of the same tissue volume is used. The grafts and controls are subcutaneously implanted for evaluation of retention, tissue morphology, and histological cross-sections during the course of 6-12 months.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

The invention claimed is:

1. A dermatological composition comprising at least one amphiphilic peptide comprising alternating hydrophobic/hydrophilic amino acid residues, or a derivative or a salt thereof, wherein the peptide comprises 1-20 pairs of hydrophobic-hydrophilic alternating amino acid residues, wherein the hydrophilic amino acid residue is selected from the group consisting of Glu, Asp, Tyr, Ser, Thr, Ser(PO$_4$), Thr(PO$_4$), and Tyr(PO$_4$), and the hydrophobic amino acid residue is selected from the group consisting of Phe, Leu, Ile, Val, Trp, and Ala, and wherein said peptide has no more than 10% positively charged amino acid residues, and a dermatologically acceptable carrier, wherein the dermatological composition is a soft tissue filler composition, and wherein the dermatological composition further comprises a plurality of cells obtained from adipose tissue.

2. The dermatological composition of claim 1, wherein the at least one amphiphilic peptide has 2 to 40 amino acids, or wherein the at least one amphiphilic peptide further comprises at least one terminal Pro residue.

3. The dermatological composition of claim 1, wherein the at least one amphiphilic peptide comprises an amino acid sequence according to Formula I:

$$\text{X-(hydrophobic-hydrophilic)}_n\text{-B} \qquad \text{(Formula I)}$$

or a salt thereof, wherein n designates an integer of 1 to 20, hydrophobic designates a hydrophobic amino acid residue selected from the group consisting of Phe, Leu, Ile, Val, Trp, and Ala, hydrophilic designates a hydrophilic amino acid residue selected from the group consisting of Glu, Asp, Tyr, Ser, Thr, Ser(PO$_4$), Thr(PO$_4$), and Tyr(PO$_4$), X designates Pro, Pro-hydrophilic or the peptide's amino terminus, and B designates Pro or the peptide's carboxy terminus; or wherein the at least one amphiphilic peptide comprises an amino acid sequence of any of the following formulae X-(Phe-Glu)$_n$-B, X-(Phe-Asp)$_n$-B, X-(Leu-Glu)$_n$-B, and X-(Leu-Asp)$_n$-B, or a salt thereof; or wherein the at least one amphiphilic peptide comprises at least one modification selected from a modification of the amino terminus X and a modification of the carboxy terminus B.

4. The dermatological composition of claim 3, wherein the modification comprises acetylation of the amino terminus, amidation of the carboxy terminus, or a combination thereof.

5. The dermatological composition of claim 1, wherein the at least one amphiphilic peptide comprises a sequence selected from the group consisting of:

```
                                          (SEQ ID NO: 1)
Pro-(Asp-Phe)5-Asp-Pro, (SEQ ID NO: 2)
Pro-Glu-(Phe-Glu)5, (SEQ ID NO: 3)
Glu-(Phe-Glu)5-Pro, (SEQ ID NO: 4)
Pro-(Ser-Phe)5-Ser-Pro, (SEQ ID NO: 5)
Pro-(SerPO4-Phe)5-SerPO4-Pro, (SEQ ID NO: 6)
Pro-(TyrPO4-Phe)5-TyrPO4-Pro,
```

-continued

```
                                          (SEQ ID NO: 7)
Pro-(Glu-Leu)5-Glu-Pro, (SEQ ID NO: 8)
Pro-(Asp-Leu)5-Asp-Pro, (SEQ ID NO: 9)
Pro-(Ser-Leu)5-Ser-Pro, (SEQ ID NO: 10)
Pro-(SerPO4-Leu)5-SerPO4-Pro, (SEQ ID NO: 11)
Pro-(TyrPO4-Leu)5-TyrPO4-Pro, (SEQ ID NO: 12)
Pro-(Glu-Phe-Ser-Phe)4-Glu-Pro, (SEQ ID NO: 13)
Pro-(SerPO4-Phe-Ser-Phe)4-Ser-Pro, (SEQ ID NO: 14)
Pro-(SerPO4-Phe-Glu-Phe)4-Glu-Pro, (SEQ ID NO: 15)
Pro-(SerPO4-Phe-Asp-Phe)4-Asp-Pro, (SEQ ID NO: 16)
Ala-Leu-Glu-(Phe-Glu)3-Pro-Ala-(Glu-Phe)3-Glu-Leu-

Pro-Ala-Leu-Glu-(Phe-Glu)3-Pro, (SEQ ID NO: 17)
Pro-Glu-(Phe-Glu)2-Lys-(Glu-Phe)2-Glu-Pro, (SEQ ID NO: 18)
Pro-Glu-(Phe-Glu)5-(Gly)3-Arg-Gly-Asp-Ser, (SEQ ID NO: 19)
(Phe-Glu)3-Pro-(Gly)3-Arg-Gly-Asp-Ser, (SEQ ID NO: 20)
Ac-Pro-Asp-(Phe-Asp)5-Pro-NH2, (SEQ ID NO: 21)
Pro-Asp-(Phe-Asp)6, (SEQ ID NO: 22)
(Phe-Asp)6, (SEQ ID NO: 23)
Pro-Glu-(Phe-Glu)5-Pro, (SEQ ID NO: 24)
Pro-Asp-(Phe-Asp)5-Pro-NH2, (SEQ ID NO: 25)
(Phe-Glu)5, (SEQ ID NO: 26)
(Phe-Glu)6, (SEQ ID NO: 27)
(Phe-Glu)7, (SEQ ID NO: 28)
Pro-Asp-(Phe-Asp)4, (SEQ ID NO: 29)
Pro-Asp-(Phe-Asp)6, (SEQ ID NO: 30)
Pro-Asp-(Phe-Asp)8, (SEQ ID NO: 31)
(Phe-Asp)5, (SEQ ID NO: 32)
(Phe-Asp)6,
```

-continued (SEQ ID NO: 33)
(Phe-Asp)$_7$, (SEQ ID NO: 34)
Pro-Asp-(Phe-Asp)$_5$-Pro-Arg-Gly-Asp-Ser, (SEQ ID NO: 35)
Pro-(Phe-Asp)$_3$-Pro,
and (SEQ ID NO: 36)
Pro-(Phe-Asp)$_3$-Pro-(Gly)$_3$-Arg-Gly-Asp-Ser, or a salt thereof.

6. The dermatological composition of claim 5, wherein the at least one amphiphilic peptide comprises a sequence as set forth in SEQ ID NO: 1, or a salt thereof.

7. The dermatological composition of claim 1, formulated for intradermal or subcutaneous administration, or formulated for use in 3D bioprinting of an artificial tissue, and/or formulated in the form of a hydrogel.

8. The dermatological composition of claim 1, further comprising at least one of hyaluronic acid, collagen, gelatin, elastin, laminin, and fibronectin.

9. The dermatological composition of claim 1, wherein the plurality of cells obtained from adipose tissue comprise adipocytes and/or adipose-derived stem cells, or wherein the plurality of cells obtained from adipose tissue are autologous; or wherein the plurality of cells obtained from adipose tissue are obtained by lipoaspiration, or wherein the plurality of cells obtained from adipose tissue are allogeneic.

10. A method of treating a soft tissue defect, the method comprising the step of injecting or implanting to a subject in need thereof an effective amount of a dermatological composition comprising at least one amphiphilic peptide comprising alternating hydrophobic/hydrophilic amino acid residues, or a derivative or a salt thereof, wherein the peptide comprises 1-20 pairs of hydrophobic-hydrophilic alternating amino acid residues, wherein the hydrophilic amino acid residue is selected from the group consisting of Glu, Asp, Tyr, Ser, Thr, Ser(PO$_4$), Thr(PO$_4$), and Tyr(PO$_4$), and the hydrophobic amino acid residue is selected from the group consisting of Phe, Leu, Ile, Val, Trp, and Ala, and wherein said peptide has no more than 10% positively charged amino acid residues, and a dermatologically acceptable carrier, wherein the dermatological composition is a soft tissue filler composition.

11. The method of claim 10, wherein treating a soft tissue defect comprises face or body contouring; or wherein treating a soft tissue defect comprises breast augmentation following mastectomy.

12. A pre-filled syringe comprising the dermatological composition of claim 1.

13. A method for treating an epidermal condition related to aging selected from the group consisting of elastosis, atrophy of the skin, fine lines, wrinkles, enlarged pores, hyperpigmentation, hypopigmentation, sagging skin, rough skin, and dry skin, or a method for treating a skin condition selected from the group consisting of cuts, wounds, burns, insect bites, jellyfish stings, a rash, skin allergic responses, and skin lesions, the method comprising the step of locally administering to a subject in need thereof an effective amount of a dermatological composition comprising at least one amphiphilic peptide comprising alternating hydrophobic/hydrophilic amino acid residues, or a derivative or a salt thereof, wherein the peptide comprises 1-20 pairs of hydrophobic-hydrophilic alternating amino acid residues, wherein the hydrophilic amino acid residue is selected from the group consisting of Glu, Asp, Tyr, Ser, Thr, Ser(PO$_4$), Thr(PO$_4$), and Tyr(PO$_4$), and the hydrophobic amino acid residue is selected from the group consisting of Phe, Leu, Ile, Val, Trp, and Ala, and wherein said peptide has no more than 10% positively charged amino acid residues, and a dermatologically acceptable carrier, wherein the dermatological composition is a cosmetic composition.

14. The method of claim 13, wherein the at least one amphiphilic peptide has 2 to 40 amino acids; or wherein the at least one amphiphilic peptide further comprises at least one terminal Pro residue; or wherein the at least one amphiphilic peptide comprises an amino acid sequence according to Formula I:

X-(hydrophobic-hydrophilic)$_n$-B (Formula I)

or a salt thereof,
wherein n designates an integer of 1 to 20, hydrophobic designates a hydrophobic amino acid residue selected from the group consisting of Phe, Leu, Ile, Val, Trp, and Ala, hydrophilic designates a hydrophilic amino acid residue selected from the group consisting of Glu, Asp, Tyr, Ser, Thr, Ser(PO$_4$), Thr(PO$_4$), and Tyr(PO$_4$), X designates Pro, Pro-hydrophilic or the peptide's amino terminus, and B designates Pro or the peptide's carboxy terminus; or wherein the at least one amphiphilic peptide comprises an amino acid sequence of any of the following formulae X-(Phe-Glu)$_n$-B, X-(Phe-Asp)$_n$-B, X-(Leu-Glu)$_n$-B, and X-(Leu-Asp)$_n$-B, or a salt thereof; or wherein the at least one amphiphilic peptide comprises at least one modification selected from a modification of the amino terminus X and a modification of the carboxy terminus B.

15. The method of claim 13, wherein the at least one amphiphilic peptide comprises a sequence selected from the group consisting of:

(SEQ ID NO: 1)
Pro-(Asp-Phe)$_5$-Asp-Pro, (SEQ ID NO: 2)
Pro-Glu-(Phe-Glu)$_5$, (SEQ ID NO: 3)
Glu-(Phe-Glu)$_5$-Pro, (SEQ ID NO: 4)
Pro-(Ser-Phe)$_5$-Ser-Pro, (SEQ ID NO: 5)
Pro-(SerPO$_4$-Phe)$_5$-SerPO$_4$-Pro, (SEQ ID NO: 6)
Pro-(TyrPO$_4$-Phe)$_5$-TyrPO$_4$-Pro, (SEQ ID NO: 7)
Pro-(Glu-Leu)$_5$-Glu-Pro, (SEQ ID NO: 8)
Pro-(Asp-Leu)$_5$-Asp-Pro, (SEQ ID NO: 9)
Pro-(Ser-Leu)$_5$-Ser-Pro, (SEQ ID NO: 10)
Pro-(SerPO$_4$-Leu)$_5$-SerPO$_4$-Pro, (SEQ ID NO: 11)
Pro-(TyrPO$_4$-Leu)$_5$-TyrPO$_4$-Pro, (SEQ ID NO: 12)
Pro-(Glu-Phe-Ser-Phe)$_4$-Glu-Pro,

-continued

```
                                     (SEQ ID NO: 13)
Pro-(SerPO4-Phe-Ser-Phe)4-Ser-Pro, (SEQ ID NO: 14)
Pro-(SerPO4-Phe-Glu-Phe)4-Glu-Pro, (SEQ ID NO: 15)
Pro-(SerPO4-Phe-Asp-Phe)4-Asp-Pro, (SEQ ID NO: 16)
Ala-Leu-Glu-(Phe-Glu)3-Pro-Ala-(Glu-Phe)3-Glu-Leu-

Pro-Ala-Leu-Glu-(Phe-Glu)3-Pro, (SEQ ID NO: 17)
Pro-Glu-(Phe-Glu)2-Lys-(Glu-Phe)2-Glu-Pro, (SEQ ID NO: 18)
Pro-Glu-(Phe-Glu)5-(Gly)3-Arg-Gly-Asp-Ser, (SEQ ID NO: 19)
(Phe-Glu)3-Pro-(Gly)3-Arg-Gly-Asp-Ser, (SEQ ID NO: 20)
Ac-Pro-Asp-(Phe-Asp)5-Pro-NH2, (SEQ ID NO: 21)
Pro-Asp-(Phe-Asp)6, (SEQ ID NO: 22)
(Phe-Asp)6, (SEQ ID NO: 23)
Pro-Glu-(Phe-Glu)5-Pro, (SEQ ID NO: 24)
Pro-Asp-(Phe-Asp)5-Pro-NH2, (SEQ ID NO: 25)
(Phe-Glu)5, (SEQ ID NO: 26)
(Phe-Glu)6, (SEQ ID NO: 27)
(Phe-Glu)7, (SEQ ID NO: 28)
Pro-Asp-(Phe-Asp)4, (SEQ ID NO: 29)
Pro-Asp-(Phe-Asp)6, (SEQ ID NO: 30)
Pro-Asp-(Phe-Asp)8, (SEQ ID NO: 31)
(Phe-Asp)5, (SEQ ID NO: 32)
(Phe-Asp)6, (SEQ ID NO: 33)
(Phe-Asp)7, (SEQ ID NO: 34)
Pro-Asp-(Phe-Asp)5-Pro-Arg-Gly-Asp-Ser, (SEQ ID NO: 35)
Pro-(Phe-Asp)3-Pro,
and (SEQ ID NO: 36)
Pro-(Phe-Asp)3-Pro-(Gly)3-Arg-Gly-Asp-Ser,
``` or a salt thereof.

16. The method of claim 15, wherein the at least one amphiphilic peptide comprises a sequence as set forth in SEQ ID NO: 1, or a salt thereof.

17. The method of claim 13, wherein the dermatological composition is formulated for topical administration in the form of a hydrogel.

18. The method of claim 10, wherein the at least one amphiphilic peptide has 2 to 40 amino acids, or wherein the at least one amphiphilic peptide further comprises at least one terminal Pro residue.

19. The method of claim 10, wherein the at least one amphiphilic peptide comprises an amino acid sequence according to Formula I:

$$X\text{-(hydrophobic-hydrophilic)}_n\text{-B(Formula I)}$$

or a salt thereof, wherein n designates an integer of 1 to 20, hydrophobic designates a hydrophobic amino acid residue selected from the group consisting of Phe, Leu, Ile, Val, Trp, and Ala, hydrophilic designates a hydrophilic amino acid residue selected from the group consisting of Glu, Asp, Tyr, Ser, Thr, Ser(PO$_4$), Thr(PO$_4$), and Tyr(PO$_4$), X designates Pro, Pro-hydrophilic or the peptide's amino terminus, and B designates Pro or the peptide's carboxy terminus; or wherein the at least one amphiphilic peptide comprises an amino acid sequence of any of the following formulae X-(Phe-Glu)$_n$-B, X-(Phe-Asp)$_n$-B, X-(Leu-Glu)$_n$-B, and X-(Leu-Asp)$_n$-B, or a salt thereof; or wherein the at least one amphiphilic peptide comprises at least one modification selected from a modification of the amino terminus X and a modification of the carboxy terminus B.

20. The method of claim 19, wherein the modification comprises acetylation of the amino terminus, amidation of the carboxy terminus, or a combination thereof.

21. The method of claim 10, wherein the at least one amphiphilic peptide comprises a sequence selected from the group consisting of:

```
                                     (SEQ ID NO: 1)
Pro-(Asp-Phe)5-Asp-Pro, (SEQ ID NO: 2)
Pro-Glu-(Phe-Glu)5, (SEQ ID NO: 3)
Glu-(Phe-Glu)5-Pro, (SEQ ID NO: 4)
Pro-(Ser-Phe)5-Ser-Pro, (SEQ ID NO: 5)
Pro-(SerPO4-Phe)5-SerPO4-Pro, (SEQ ID NO: 6)
Pro-(TyrPO4-Phe)5-TyrPO4-Pro, (SEQ ID NO: 7)
Pro-(Glu-Leu)5-Glu-Pro, (SEQ ID NO: 8)
Pro-(Asp-Leu)5-Asp-Pro, (SEQ ID NO: 9)
Pro-(Ser-Leu)5-Ser-Pro, (SEQ ID NO: 10)
Pro-(SerPO4-Leu)5-SerPO4-Pro, (SEQ ID NO: 11)
Pro-(TyrPO4-Leu)5-TyrPO4-Pro, (SEQ ID NO: 12)
Pro-(Glu-Phe-Ser-Phe)4-Glu-Pro,
```

-continued (SEQ ID NO: 13)
Pro-(SerPO$_4$-Phe-Ser-Phe)$_4$-Ser-Pro, (SEQ ID NO: 14)
Pro-(SerPO$_4$-Phe-Glu-Phe)$_4$-Glu-Pro, (SEQ ID NO: 15)
Pro-(SerPO$_4$-Phe-Asp-Phe)$_4$-Asp-Pro, (SEQ ID NO: 16)
Ala-Leu-Glu-(Phe-Glu)$_3$-Pro-Ala-(Glu-Phe)$_3$-Glu-Leu- Pro-Ala-Leu-Glu-(Phe-Glu)$_3$-Pro, (SEQ ID NO: 17)
Pro-Glu-(Phe-Glu)$_2$-Lys-(Glu-Phe)$_2$-Glu-Pro, (SEQ ID NO: 18)
Pro-Glu-(Phe-Glu)$_5$-(Gly)$_3$-Arg-Gly-Asp-Ser, (SEQ ID NO: 19)
(Phe-Glu)$_3$-Pro-(Gly)$_3$-Arg-Gly-Asp-Ser, (SEQ ID NO: 20)
Ac-Pro-Asp-(Phe-Asp)$_5$-Pro-NH$_2$, (SEQ ID NO: 21)
Pro-Asp-(Phe-Asp)$_6$, (SEQ ID NO: 22)
(Phe-Asp)$_6$, (SEQ ID NO: 23)
Pro-Glu-(Phe-Glu)$_5$-Pro, (SEQ ID NO: 24)
Pro-Asp-(Phe-Asp)$_5$-Pro-NH$_2$, (SEQ ID NO: 25)
(Phe-Glu)$_5$, (SEQ ID NO: 26)
(Phe-Glu)$_6$, (SEQ ID NO: 27)
(Phe-Glu)$_7$, (SEQ ID NO: 28)
Pro-Asp-(Phe-Asp)$_4$, (SEQ ID NO: 29)
Pro-Asp-(Phe-Asp)$_6$, -continued (SEQ ID NO: 30)
Pro-Asp-(Phe-Asp)$_8$, (SEQ ID NO: 31)
(Phe-Asp)$_5$, (SEQ ID NO: 32)
(Phe-Asp)$_6$, (SEQ ID NO: 33)
(Phe-Asp)$_7$, (SEQ ID NO: 34)
Pro-Asp-(Phe-Asp)$_5$-Pro-Arg-Gly-Asp-Ser, (SEQ ID NO: 35)
Pro-(Phe-Asp)$_3$-Pro,
and (SEQ ID NO: 36)
Pro-(Phe-Asp)$_3$-Pro-(Gly)$_3$-Arg-Gly-Asp-Ser, or a salt thereof.

22. The method of claim 21, wherein the at least one amphiphilic peptide comprises a sequence as set forth in SEQ ID NO: 1, or a salt thereof.

23. The method of claim 10, wherein the dermatological composition is formulated for intradermal or subcutaneous administration, or wherein the dermatological composition is formulated for use in 3D bioprinting of an artificial tissue, and/or wherein the dermatological composition is in the form of a hydrogel.

24. The method of claim 10, wherein the dermatological composition further comprises at least one of hyaluronic acid, collagen, gelatin, elastin, laminin, and fibronectin.

25. The method of claim 10, wherein the dermatological composition further comprises a plurality of cells obtained from adipose tissue.

26. The method of claim 25, wherein the plurality of cells obtained from adipose tissue comprise adipocytes and/or adipose-derived stem cells, or wherein the plurality of cells obtained from adipose tissue are autologous; or wherein the plurality of cells obtained from adipose tissue are obtained by lipoaspiration, or wherein the plurality of cells obtained from adipose tissue are allogeneic.

* * * * *